(12) United States Patent
Suh et al.

(10) Patent No.: US 8,377,715 B2
(45) Date of Patent: Feb. 19, 2013

(54) METHOD AND DEVICE FOR SAMPLE PREPARATION

(75) Inventors: Chris Suh, San Jose, CA (US); Lee Hoang, Santa Clara, CA (US); Jennifer E. Grant, Los Gatos, CA (US); Douglas T. Gjerde, Saratoga, CA (US)

(73) Assignee: PhyNexus, Inc., San Jose, CA (US)

( * ) Notice: Subject to any disclaimer, the term of this patent is extended or adjusted under 35 U.S.C. 154(b) by 48 days.

(21) Appl. No.: 12/767,659

(22) Filed: Apr. 26, 2010

(65) Prior Publication Data

US 2010/0200509 A1    Aug. 12, 2010

Related U.S. Application Data

(63) Continuation-in-part of application No. 11/285,531, filed on Nov. 21, 2005, now Pat. No. 7,722,820, which is a continuation-in-part of application No. 10/754,352, filed on Jan. 8, 2004, now abandoned, which is a continuation-in-part of application No. 10/620,155, filed on Jul. 14, 2003, now Pat. No. 7,482,169.

(51) Int. Cl.
*G01N 1/18* (2006.01)

(52) U.S. Cl. ........ 436/177; 436/178; 436/161; 422/524; 422/535; 422/534; 422/527

(58) Field of Classification Search ............... 422/502, 422/524, 535, 534, 527; 436/161, 177, 178
See application file for complete search history.

(56) References Cited

U.S. PATENT DOCUMENTS

| | | | | |
|---|---|---|---|---|
| 5,437,979 A | * | 8/1995 | Rampal et al. | 435/6.16 |
| 5,747,663 A | | 5/1998 | Colpan et al. | |
| 5,833,927 A | * | 11/1998 | Raybuck et al. | 422/513 |
| 5,888,831 A | * | 3/1999 | Gautsch | 436/177 |
| 5,990,301 A | * | 11/1999 | Colpan et al. | 536/25.4 |
| 6,180,778 B1 | | 1/2001 | Bastian et al. | |
| 6,242,220 B1 | | 6/2001 | Wahle et al. | |
| 6,274,371 B1 | | 8/2001 | Colpan | |
| 6,277,648 B1 | | 8/2001 | Colpan | |
| 6,297,371 B1 | | 10/2001 | Colpan et al. | |
| 6,383,393 B1 | | 5/2002 | Colpan et al. | |
| 6,821,757 B2 | | 11/2004 | Sauer et al. | |
| 6,946,250 B2 | | 9/2005 | Bastian et al. | |
| 7,074,916 B2 | | 7/2006 | Bastian et al. | |
| 2006/0124551 A1 | * | 6/2006 | Gjerde et al. | 210/656 |

OTHER PUBLICATIONS

QIAprep Miniprep Handbook, 2nd Ed. Dec. 2006.

* cited by examiner

*Primary Examiner* — Krishnan S Menon
*Assistant Examiner* — Dwan A Gerido
(74) *Attorney, Agent, or Firm* — Sue S. Kalman

(57) ABSTRACT

The invention provides pipette tip extraction columns for the purification of a DNA vector from un-clarified cell lysate containing cell debris as well as methods for making and using such columns. The columns typically include a bed of extraction media positioned in the pipette tip column, above a bottom frit and with an optional top frit.

7 Claims, 6 Drawing Sheets

METHOD AND DEVICE FOR SAMPLE PREPARATION

CROSS REFERENCE TO RELATED APPLICATIONS

This application is a continuation-in-part of U.S. Patent Application 11/285,531 filed Nov. 21, 2005, now U.S. Pat. No. 7,722,820, which is a continuation-in-part of U.S. patent application Ser. No. 10/754,352 filed Jan. 8, 2004, now abandoned, which is a continuation-in-part of U.S. patent application Ser. No. 10/620,155 filed Jul. 14, 2003, now U.S. Pat No. 7,482,169.

FIELD OF THE INVENTION

This invention relates to methods and devices for sample preparation, such as separating (i.e., extracting or purifying) DNA vectors. The device and method of this invention are particularly useful in DNA vector purification by pipette tip column. The device and method of this invention are particularly useful in purifying plasmids from un-clarified cell lysates and other samples containing particulates and cell debris.

BACKGROUND OF THE INVENTION

DNA vectors, including bacterial plasmids, are found naturally along with genomic DNA in prokaryotes and sometimes in eukaryotic organisms. Plasmids are double-stranded, circular DNA molecules that replicate within a cell independently of chromosomal or genomic DNA of the cell. Plasmid size can vary from 1 K base pairs to over 1,000 K base pairs. Plasmids contained within a cell are identical. However, the numbers of plasmid copies within a particular cell can range anywhere from a single unit to several thousand copies.

One way to classify plasmids is by function. Fertility-F-plasmids, which contain tra-genes, are capable of conjugation (transfer of genetic material between bacteria which are touching). Resistance-(R)-plasmids contain genes that can build a resistance against antibiotics or poisons and help bacteria produce pili. Col-plasmids contain genes that code for bacteriocins, proteins that can kill other bacteria. Degradative plasmids enable the digestion of unusual substances, e.g., toluene or salicylic acid. Virulence plasmids turn the bacterium into a disease causing pathogen.

Plasmid DNA can appear in different conformations. These include "Nicked Open-Circular" DNA with one strand cut. "Relaxed Circular" DNA is fully intact with both strands uncut, but has been enzymatically "relaxed" (supercoils removed). "Linear" DNA has free ends, either because both strands have been cut, or because the DNA was linear in vivo. "Supercoiled" (or "Covalently Closed-Circular") DNA is fully intact with both strands uncut, and with a twist built in, resulting in a compact form. "Supercoiled Denatured" DNA is like supercoiled DNA, but has unpaired regions that make it slightly less compact; this can result from excessive alkalinity during plasmid preparation.

Plasmids serve as important tools in genetics and biotechnology labs where they are used in genetic engineering to duplicate DNA sequences or generate new sequences. Plasmids are commonly used to multiply (make many copies of) or express particular genes. Another major use of plasmids is to make large amounts of proteins. In this case, researchers grow bacteria containing a plasmid harboring the gene of interest, which can be induced to produce large amounts of proteins from the inserted gene.

Plasmids in this form are called vectors and are considered transferable genetic elements of cells. They are capable of autonomous replication and expression if placed within a suitable host. Plasmid host-to-host transfer requires direct, mechanical transfer allowing the intentional uptake of the genetic element by transformation into the host. Restriction enzymes are frequently used to specifically cut the plasmid DNA at specific short sequences in open plasmids and insert short sequences of DNA. The inserts can have a number of functions including coding for the production of a particular and desired protein. When researchers manipulate DNA vectors in this manner, it is sometimes called a DNA construct since the researcher has generated a customized DNA sequence.

DNA vectors have been discovered in nature and used the research laboratory as a molecular biology tool. DNA vectors have been classified according to host organism and the origin of the extrachromosomal DNA molecules. When these vectors are used to harbor DNA sequences of interest, these vectors are called cloning vectors. Plasmids are autonomously replicating DNA molecules from bacteria. Plasmids can be engineered to maintain and replicate DNA sequences of interest. These sequences are inserted into the plasmid and the size of the insert is restricted by the type of cloning vector. Plasmids can contain inserts sizes of 1 to 200 kb. Viruses that attack bacteria, bacteriophage, can insert its chromosome into the host bacteria. The bacteria's cellular machinery is then instructed to replicate many copies of the bacteriophage. Researchers have taken advantage of this biology to generate a cloning vector from bacteriophage, which can be used to carry DNA insert sizes up to 16 kb. Taking advantage of the Lambda phage replication system, a plasmid based upon Lambda's replication machinery has been generated called a cosmid. Cosmids can carry up to 25 kp of DNA. Large vectors can be generated from the bacteria fertility plasmid. When these fertility plasmids are generated as engineered DNA constructs, they are called Bacteria Artificial Chromosomes (BACs) and can maintain insert sizes of 150-350 kb. A similar manipulation can be achieved in yeast in which an artificial yeast chromosome is generated. These are called Yeast Artificial Chromosomes (YACs) and can contain DNA inserts between 100 kb and 3,000 kb.

In addition to cloning vectors, many DNA vectors have been used as a method for DNA delivery. When DNA vectors are introduced in bacterial cells, non-animal eukaryotes and plant cells, this is called transformation. Using non-viral methods, such as chemical or electroporation to introduce DNA vectors into eukaryotic cells is called transfection. There are viral methods to introduce DNA vectors into animal cells, which are called transduction. With the ability to use many systems to propagate a DNA vector and transfer it to different organisms, it is important to be able to recover the DNA vectors from all of these different systems. DNA vectors can be isolated from cell lysate of prokaryotes, eukaryote and archea. DNA vectors can also be isolated from cell culture systems such as mammalian and insect cell systems.

In order to manipulate and use DNA vectors for molecular cloning, they often need to be isolated and purified from a cell or cell culture. Current technology tools used to isolate and purify plasmids include the use of solid phase extraction plates, spin columns and magnetic beads. Due to the complexity of the purification process, procedures using these tools consist of a combination of several manual and automated steps.

To start, DNA vectors or plasmids are grown in cell cultures over several hours under controlled heat and nutrient growth conditions. After cell culture growth is complete, the first step in the process is to recover the cells into a pellet. The cells are spun down and cleaned, removing the growth medium and any extra cell culture debris and material. At this point, the cell pellet is re-suspended in a buffer and then is mixed with a lysing solution to break up the cell walls and release the plasmids. An RNase is usually included to digest any RNA that may be present so that it is not captured and purified with the plasmid in later steps. After lysing, the mixture is neutralized. The resulting mixture consists of plasmid, genomic DNA, proteins, cell debris and other miscellaneous materials. The lysing and neutralization process must be performed gently in order to prevent or limit shearing of the genomic DNA. Genomic DNA is large and in effect chemically different from DNA vectors, but sheared genomic DNA may mimic plasmid in subsequent steps and could be captured and contaminate the final recovered DNA vector product. Once the lysing and neutralization steps are completed, the mixture is usually clarified with another spin down step to remove cell debris and genomic material.

At this point, columns, plates or magnetic beads containing a solid extraction phase are used in a series of automated or manual steps to recover the DNA vector from the clarified lysate. Complete automation of the process is not performed mainly because of the need to remove the cellular debris from the sample. There exists a need to reduce the manual manipulation of DNA vector purification.

Solid phase extraction is a powerful technology for purifying and concentrating biomolecules including DNA vectors and including plasmids. Sample preparation methods are needed to permit the automated purification and concentration of DNA vectors. This is difficult because of the presence of cellular debris in the samples. Not only can particulate plug columns but extraneous sample material can interfere with the selective capture of the DNA vector or be co-captured. Spin column methods and magnetic beads process samples from clarified cell lysates where the cell debris is removed from the sample with centrifugation prior to sample processing. The subject invention involves methods and devices for extracting and recovering DNA vectors from a sample using a bed of extraction media contained in a pipette tip column. These methods, and the related devices and reagents, will be of particular interest to the life scientist, since they provide a powerful technology for purifying, concentrating, analyzing and using plasmids and other biomolecules of interest from biological samples including cell culture and in particular un-clarified cell lysates. The methods, devices and reagents can find wide application in a variety of preparative, genetic engineering and analytical contexts.

SUMMARY OF THE INVENTION

There are many issues preventing development of a fully automated DNA vector purification method. For example, particulates will easily plug columns. This is especially true for pipette tip columns. While pipette columns can tolerate some particulates they have not been able to tolerate samples containing biological debris, cell debris and cell lysate particulates. For example, we found that all pipette tip columns with 37 um pore size membrane screen frits will plug immediately from cell debris found in un-clarified cell lysates. This was found to be completely independent of the particle size of the material that was packed in the column. Pipette and liquid handlers have very low pressure to force liquids through a pipette tip column. Unlike spin columns that have thousands of psi pressures of force available to apply to the liquid above the column or vacuum plates that apply 5-1 psi and higher pressure differentials, pipette and liquid handlers operate at less than 5 psi pressures and vacuums and often much less than 1 psi pressures and vacuums. These pumping low forces were found not to be able to overcome the tendency for pipette tip columns to plug with cell lysate debris. Even a small amount of clogging or partial plugging of the pipette tip column prevented the complete cycling of liquid through the columns and prevented purification.

It was not known whether prevention of liquid flow through the column was because of insufficient pumping pressure, too small of frit pore size, too few frit holes, the ability of the column packing material to act as a particle filter, all of these factors, a combinations of these factors, or some other unknown issue such as the sticking of particles to the various surfaces. Increasing the frit pore size to reduce plugging of the column is not the logical because this creates the need to increase the particle packing size to prevent loss of the packing material. Larger beads have lower surface per unit volume. The interaction of DNA with resin is a surface phenomenon because DNA is large and can only interact with the surface of a bead. For a given bed volume, increasing the bead size substantially decreases the available surface for capture. Silica membrane spin columns and plates have very small particles sizes.

Even if particulates could pass through the column bed, the particulates in the sample could provide competing surface for DNA vector interaction and prevent capture by the resin. Particulates could interact with the resin surface and prevent capture of the DNA vectors.

Passing particulates containing genomic DNA through a backed bed could shear the genomic DNA in the column bed or around the beads. The reason for this concern is lysed cell cultures must be treated gently to prevent shearing of long DNA molecules. The forces applied to genomic DNA are unknown and unpredictable while traveling through a packed bed column. However, small DNA fragments formed from sheared DNA, if formed, will chemically mimic plasmid DNA and can be captured, washed and recovered along side the plasmid molecules. Forcing genomic DNA through a column could either plug the column or shear the genomic DNA or both plug or shear. Even if the column is not plugged, the shearing process would be unpredictable, especially with multiple passes through a column frit and bed. It was possible, even likely, that genomic DNA would simply stick to the various surfaces and then release unpredictably during the purification process.

By gradually increasing the frit pore size and increasing the packing particle size, pausing at the end of the each pumping cycle so that the flow could catch up to the pump stroke, we were able to get some flow of un-clarified e-coil cell lysate through the column. In some cases, the tip of the column had to be positioned to the middle part of the sample well away from the bulk of the particulate, which tended to either float or sink. If care was taken to prevent the cell lysate particulates that either floated or sunk to the bottom, it was found that pore sizes greater than 50 um pores were able to get flow of liquids containing of cell lysate debris through the pipette tip columns. Later, as the column diameter was increased, 33 μm pore size frits were found to be able to tolerate some cell lysate particulates.

Even after achieving some initial flow of cell lysate particulate containing samples, the initial work provided very poor recovery of plasmids form un-clarified cell lysate. Side by side processing of an identical clarified sample with a commercial spin column produced usable quantities of plasmids at will. Initially it was reasoned to be due to poor plasmid capture for the reasons stated above. Experiments continued over many weeks where the amount of resin was increased, the type of resin studied, and the residence time or the number of flow cycles increased. Improvement was very limited. Finally, although unlikely, it thought to be possible that the poor recovery was not due to poor capture but from poor elution from the resin. The plasmid was possibly actually being captured by the resin, but was not being removed in the elution. This was impossible to measure because due to the particulates, it was impossible to determine the amount of plasmid in the column flow through.

Surprisingly, we were able to increase recovery by modifying the wash procedure. In our initial work we tried to capture plasmids onto a silica surface with chaotropic reagents in the unclarified cell lysate solution/suspension. In hindsight, it was discovered that chaotropic reagents are difficult to remove from a pipette tip column with back and forth flow. While it is difficult to get sufficient plasmids to stick to the low surface area (large) silica bead, once they do stick they are difficult to remove from a pipette tip column because residual chaeotropic reagents or alcohols in the elution solvent prevented elution. This was only determined after the fact by changing the wash procedure to first wash with a chaotropic salt, then washing with an alcohol and then finally eluting with sufficient volume of solvent so that any residual alcohol did not interfere with the elution process. Also, eluting in several steps with several aliquots of liquid improved recovery of the plasmid. It was found that with back and forth flow through pipette tip columns, it is difficult to remove all of the previous solution and several washes are needed. If residual chaotropic solvents or alcohols are present, elution of the plasmid will be incomplete. Spin columns or filter columns rely on single direction flow and high forces to remove residual liquids. This more complete removal of the wash solvents allows more complete elution of the DNA vector from the column. Pipette tip columns must rely on multiple washes and large liquid volumes to bed volume to wash the resin. Washing must be performed correctly to remove as much solvent as possible.

Columns and methods for purifying plasmids DNA from *E. coli* lysate was developed for 96 at a time sample format. The method was designed to operate on a Tecan EVO, Biomek FX and other robotic liquid handlers. The yield was greater than 5 μg per well and was transformation/transfection quality DNA with no RNA contamination. The purity was examined with slab gel electrophoresis and UV absorption with A260/A280 ratio between 1.8- and 2.0.

The Procedure Developed was as Follows.
1. Add 250 μL of Lysis buffer to resuspended cells using gentle pipette mixing for 3 minutes.
2. Add 350 μL of Neutralization buffer to lysed culture using gentle pipette mixing for 3 minutes.
3. Attach plasmid DNA PhyTip columns to 96 channel head.
4. Equilibrate the PhyTip columns by cycling through the equilibration buffer (2.8 min).
   Use 2 cycles at 0.5 mL/min flow rate.
5. Capture the plasmid DNA (50 min).
   Use 24 cycles at 0.25 mL/min flow rate.
6. Wash (Wash 1 buffer, 500 μL) the captured plasmid DNA (2.8 min).
   Use 2 cycles at 0.5mL/min flow rate.
7. Wash (Wash2 buffer, 500 μL) the captured plasmid DNA (2.8 min).
   Use 2 cycles at 0.5 mL/min flow rate.
8. Wash (Wash2 buffer, 500 μL) the captured plasmid DNA (2.8 min).
   Use 2 cycles at 0.5 mL/min flow rate.
9. Blowout remaining wash buffer.
10. Elute the captured plasmid DNA (33 min).
    Use 16 cycles at 0.25 mL/min flow rate.
Total time ~95 min The columns used in this example were 80 μL bed columns fitted with 100 μm pore size screen bottom frits. Columns were packed with and without a top screen frit of 100 μm pore size. The top frit was fitted directly above the column, with a 2-3 mm spacing above the column and with a 15-20 mm spacing above the column bed. Columns contained several types of resin including Chromasorb P material purchased from Sigma Aldrich.

A side by side comparison with Qiagen spin columns was made using buffers listed in Table A. Overnight *E. coli* 1.4 mL growth in a 96 deep well plate were used as samples. The results of three representative samples are shown in Table B.

TABLE A

Buffers

| Buffer Name | Content |
| --- | --- |
| Resuspension buffer | 50 mM Tris-HCl pH8.0, 10 mM EDTA, 100 ug/mL Rnase A |
| Lysis buffer | 200 mM NaOH, 1% SDS |
| Neutralization buffer | 4.2M guanidine hydrochloride 0.9M Potassium acetate pH4.8 |
| Equilibration buffer | 7M Gu-HCL pH 5.5 |
| Wash1 buffer | 5M guanidine hydrochloride 30% Ethanol, 10 mM TRIS-HCl pH 6.6 |
| Wash2 buffer | 10 mM TRIS-HCl pH 7.5, 80% Ethanol |
| Elution buffer | Water |

TABLE B

Representative results of purification of plasmid using Qiagen spin column and two types of pipette tip columns.

| Column Name | A260 | Conc (ng/μL) | A260/A280 | Total μg | Combined total μg |
| --- | --- | --- | --- | --- | --- |
| Qiagen E1 (100 μL elution) | 0.86 | 43.05 | 1.78 | 4.30 | |
| Qiagen E2 (100 μL elution) | 0.19 | 9.6 | 1.63 | 0.96 | |
| Qiagen E3 (100 μL elution) | 0.14 | 7.05 | 1.10 | 0.70 | 5.97 |
| PhyTip [top frit] E1 (100 μL) | 1.12 | 56.2 | 1.97 | 5.62 | |
| PhyTip [top frit] E2 (100 μL) | 0.51 | 25.5 | 1.93 | 2.55 | |
| PhyTip [top frit] E3 (100 μL) | 0.28 | 14.25 | 1.73 | 1.42 | 9.59 |
| PhyTip [no top frit] E1 (100 μL) | 0.61 | 30.75 | 1.92 | 3.07 | |
| PhyTip [no top frit] E2 (100 μL) | 0.64 | 31.95 | 1.92 | 3.19 | |
| PhyTip no [top frit] E3 (100 μL) | 0.37 | 18.55 | 1.80 | 1.85 | 8.12 |

E1, E2 and E3 refer to the recovery from three sequential elution aliquots.

Purification using silica is based on a bind-wash-elute procedure. DNA vectors are adsorbed to the silica media in the presence of chaotropic salts, which remove water from hydrated molecules in solution. Polysaccharides and proteins do not adsorb and are removed. After several wash steps, pure DNA vector material is eluted under low- or no-salt conditions ready for immediate use.

Several silica resins can be packed into the column. Celite and diatomaceous earth have very high back pressure since they are smaller. Davisil Silica Gel, Silica Gel Imapaq, Biotage Silica Gel work. Chromosorb P is large and works well. Silicon Quartz also works although the capacity is lower.

Other chemistries that can be used with this invention include ion exchange, affinity and others listed in Tables C and D.

The invention provides columns, many of which are characterized by the use of relatively small beds of extraction media. In one embodiment, the instant invention provides a sample pipette tip column comprising a column body having an open upper end, an open lower end, and an open channel between the upper and lower ends of the column body; a bottom frit bonded to and extending across the open lower end and a bed of extraction media positioned inside the open channel above the bottom frit.

In certain embodiments, an optional top frit may be employed. For example, in some embodiments, the invention provides an extraction column comprising: a pipette tip column body having an open upper end, an open lower end, and an open channel between the upper and lower end of the column body; a bottom frit bonded to and extending across the open channel; a top frit bonded to and extending across the open channel between the bottom frit and the open upper end of the column body, wherein the top frit, bottom frit, and column body define an extraction media chamber; and a bed of extraction media positioned inside the extraction media chamber. The position of the top frit over the bead may just touch the top of the resin bed or be positioned substantially above the resin bed. When the frit is above the resin bed, the resin bed may move or expand with aspiration of liquids including the sample containing the particulates. The bed may move down against the bottom frit with expulsion of the liquid.

In some embodiments the frit material is a porous membrane having large pores.

In some embodiments the frit material is a membrane screen having large pores

In some embodiments the frit material is a wad of fiber or porous material of glass, polymer, metal, or other material having large pores.

In some embodiments the frit material is a sintered polymer, glass, ceramic or metal having large pores.

In some embodiments, the bed of extraction media comprises a packed bed of resin beads. Non-limiting examples of resin beads include gel resins, pellicular resins and macroporous resins.

In certain preferred embodiments of the invention, the column comprises a packed bed of silica, cellulose, agarose or polymer resin beads.

In certain embodiments of the invention, the bottom frit and/or the top frit is/are a membrane screen, e.g., a polypropylene or polyester membrane.

In certain embodiments of the invention, the bed of extraction media has a volume of between about 1 µL and 1000 µL, between about 1 µL and 100 µL, between about 1 µL and 20 µL, between about 1 µL and 10 µL, or between about 3 µL and 10 µL.

In certain embodiments of the invention, the bottom frit and/or the top frit is/are less than 200 or less than 1000 microns thick.

In certain embodiments of the invention, the bottom frit and/or the top frit is/are less than 5 mm thick and less than 10 mm thick.

In certain embodiments of the invention, the bottom frit and/or the top frit has/have a pore volume equal to 10% or less of the interstitial volume of the bed of extraction media.

In certain embodiments of the invention, the bottom frit and/or the top frit has/have a low pore volume.

In certain embodiments of the invention, the bottom frit and/or the top frit has/have a large pore size.

In certain embodiments of the invention, the bottom frit and/or the top frit has/have a large pore size sufficient to allow cell debris or other particulates to flow through the frit without clogging or plugging under low pressures applied by a pipette or liquid handler.

In certain embodiments of the invention, the extraction media comprises a surface or binding group having an affinity for nucleic acid e.g., silica, polymer, ion exchanger, nucleic acid and Streptavidin.

In certain embodiments of the invention, the column body comprises a polycarbonate, polypropylene or polyethylene material.

In certain embodiments of the invention, the column body comprises a luer adapter, a syringe or a pipette tip.

In certain embodiments of the invention, the upper end of the column body is attached to a pump for aspirating fluid through the lower end of the column body, e.g. a pipettor, a syringe, a peristaltic pump, a pressure and/or vacuum pump.

In certain embodiments of the invention, the column comprises a lower tubular member comprising: the lower end of the column body, a first engaging end, and a lower open channel between the lower end of the column body and the first engaging end; and an upper tubular member comprising the upper end of the column body, a second engaging end, and an upper open channel between the upper end of the column body and the second engaging end, the top membrane screen of the extraction column bonded to and extending across the upper open channel at the second engaging end; wherein the first engaging end engages the second engaging end to form a sealing engagement. In some of these embodiments, the first engaging end has an inner diameter that matches the external diameter of the second engaging end, and wherein the first engaging end receives the second engaging end in a telescoping relation. The first engaging end optionally has a tapered bore that matches a tapered external surface of the second engaging end.

The invention further provides a method for extracting an analyte from a sample solution comprising the steps of introducing a plasmid sample solution into the bed of extraction media of an extraction column of the invention, wherein the extraction media comprises an binding group or surface having an affinity for the plasmids, whereby at least some fraction of the plasmid is adsorbed or captured by the extraction media; substantially evacuating the sample solution from the bed of extraction media, leaving the adsorbed plasmid bound to the extraction media; introducing a desorption solvent into the bed of extraction media, whereby at least some fraction of the bound plasmid is desorbed from the extraction media into the desorption solvent; and eluting the desorption solvent containing the desorbed analyte from the bed of extraction media.

In certain embodiments of the method, the extraction column is attached to a pump at one end and one or more of the solvents, e.g., the desorption solvent and/or the sample solution, is aspirated and discharged through the lower end of the column.

In certain embodiments of the method, the extraction media is washed between the sample loading and desorption steps.

In certain embodiments of the method, the sample, wash and or desorption solvents are aspirated and discharged from the column more than once, i.e., a plurality of in/out cycles are employed to pass the solvent back and forth through the bed more than once.

In certain embodiments of the method, prior to the desorption step, a gas is passed through the bed of extraction media, resulting in the evacuation of a majority of bulk liquid residing in said interstitial volume. The bulk liquid can comprise sample solution and/or wash solution. The gas can comprise of air or nitrogen.

DESCRIPTION OF SPECIFIC EMBODIMENTS OF THE INVENTION

Figure 1:
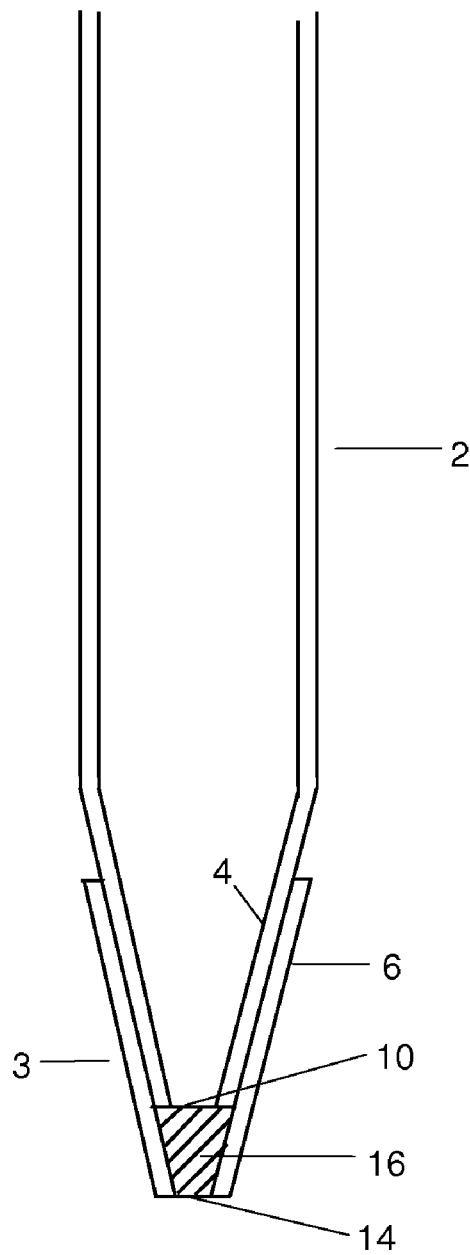
FIG. 1 depicts an embodiment of the invention where the extraction column body is constructed from a tapered pipette tip.

This invention relates to methods and devices for extracting DNA vector plasmids from a sample solution. In U.S. patent application Ser. No. 10/620,155, incorporated by reference herein in its entirety, methods and devices for performing low dead column extractions are described. The instant specification, inter alia, expands upon the concepts described in that application.

Before describing the present invention in detail, it is to be understood that this invention is not limited to specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like.

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, specific examples of appropriate materials and methods are described herein.

Definitions

In describing and claiming the present invention, the following terminology will be used in accordance with the definitions set out below.

The term "bed volume" as used herein is defined as the volume of a bed of extraction media in an extraction column. Depending on how densely the bed is packed, the volume of the extraction media in the column bed is typically about one third to two thirds of the total bed volume; well packed beds have less space between the beads and hence generally have lower interstitial volumes.

The term "interstitial volume" of the bed refers to the volume of the bed of extraction media that is accessible to solvent, e.g., aqueous sample solutions, wash solutions and desorption solvents. For example, in the case where the extraction media is a chromatography bead (e.g., agarose or sepharose), the interstitial volume of the bed constitutes the solvent accessible volume between the beads, as well as any solvent accessible internal regions of the bead, e.g., solvent accessible pores. The interstitial volume of the bed represents the minimum volume of liquid required to saturate the column bed.

The term "dead volume" as used herein with respect to a column is defined as the interstitial volume of the extraction bed, tubes, membrane or frits, and passageways in a column. Some preferred embodiments of the invention involve the use of low dead volume columns, as described in more detail in U.S. patent application Ser. No. 10/620,155.

The term "elution volume" as used herein is defined as the volume of desorption or elution liquid into which the analytes are desorbed and collected. The terms "desorption solvent," "elution liquid" and the like are used interchangeably herein.

The terms "extraction column" and "extraction tip" and "pipette tip column" as used herein are used interchangeably and defined as a column device used in combination with a pump, the column device containing a bed of solid phase extraction material, i.e., extraction media. The preferred mode of pumping is back and forth flow pumping through the end of the column.

The term "frit" as used herein are defined as porous material for holding the extraction media in place in a column. An extraction media chamber is typically defined by and the area over a bottom frit positioned in an extraction column. In preferred embodiments of the invention, the frit is a thin, low pore volume, large pore screen.

The term "lower column body" as used herein is defined as the column bed and bottom membrane screen of a column.

The term "membrane screen" as used herein is defined as a woven or non-woven fabric or screen for holding the column packing in place in the column bed. The membranes are of sufficient strength to withstand packing and use of the column bed and of sufficient porosity to allow passage of liquids and particulate into the column bed.

The term "sample volume" as used herein is defined as the volume of the liquid of the original sample solution from which the analytes are separated or purified.

The term "upper column body" as used herein is defined as the chamber and top membrane screen of a column.

The term "pipette column tip" as used herein is defined as any column containing a bed of media that can be fitted to a pipette or syringe or liquid handler.

The term "DNA vectors" and "plasmid" and "plasmid DNA" and "shuttle vector" and "cloning vector" as used herein are used interchangeably are defined as autonomously replicating DNA molecules. These molecules are usually double stranded, can be circular and vary in size between 100 base pairs to over 3,000,000 base pairs. Features of the molecule consist of the ability to replicate independently of the host cell's genome. Other features include a site amenable to insertion and maintenance of double stranded DNA sequences. The molecule will also consist of features that allow the molecule to be maintained and propagated in the host cell. DNA vectors can exist in hosts of different species.

The term "sample matrix" as used herein is defined as any sample from which DNA vectors are or can be present. These include but are not limited to prokaryote cells, eukaryote cells and archea cells.

The term "lyse" and "lysis" and "lysing" as used herein are used interchangeably is defined as interruption of the cell membrane or plasma membrane. When present, the cell wall is disrupted prior to or during cell membrane disruption. The disruption of the cell membrane releases the contents of the cell's cytoplasm. The extent of cell membrane disruption can contents of nuclei, organelles and any structure composed of a phospholipid bilayer. Lysis procedures consist of and are not limited to chemical and physical disruption of the cell membrane.

Extraction Columns

In accordance with the present invention, there may be employed extraction chemistry. Extraction chemistry media is similar to chromatography media except in extraction, only a single equilibrium is achieved in each step. In chromatography, multi equilibrium reactions are used to separate materials. Therefore, interaction of the sample and other materials with the resin have large and distinct differences in selectivity coefficients. Chromatography and extraction are two different types of separation processes. Yet materials for extractions are described in the chromatography literature. See, e.g.

*Chromatography*, 5$^{th}$ edition, PART A: FUNDAMENTALS AND TECHNIQUES, editor: E. Heftmann, Elsevier Science Publishing Company, New York (1992); ADVANCED CHROMATOGRAPHIC AND ELECTROMIGRATION METHODS IN BIOSCIENCES, editor: Z. Deyl, Elsevier Science BV, Amsterdam, The Netherlands, (1998); CHROMATOGRAPHY TODAY, Colin F. Poole and Salwa K. Poole, and Elsevier Science Publishing Company, New York, (1991).

In some embodiments of the subject invention, the packed bed of extraction media is contained in a column, e.g., large frit pore size column. Non-limiting examples of suitable columns, particularly low dead volume columns, large frit pore size are presented herein. It is to be understood that the subject invention is not to be construed as limited to the use of extraction beds in low dead volume columns, or in columns in general. For example, the invention is equally applicable to use with a packed bed of extraction media as a component of a multi-well plate.

Column Body

The column body is a tube having two open ends connected by an open channel, sometimes referred to as a through passageway. The tube can be in any shape, including but not limited to cylindrical or frustoconical, and of any dimensions consistent with the function of the column as described herein. In some preferred embodiments of the invention, the column body takes the form of a pipette tip, a syringe, a luer adapter or similar tubular bodies. In embodiments where the column body is a pipette tip, the end of the tip wherein the bed of extraction media is placed can take any of a number of geometries, e.g., it can be tapered or cylindrical. In some case a cylindrical channel of relatively constant radius can be preferable to a tapered tip, for a variety of reason, e.g., solution flows through the bed at a uniform rate, rather than varying as a function of a variable channel diameter.

In some embodiments, one of the open ends of the column, sometimes referred to herein as the open upper end of the column, is adapted for attachment to a pump, either directly or indirectly. In some embodiments of the invention, the upper open end is operatively attached to a pump, whereby the pump can be used for aspirating (i.e., drawing) a fluid into the extraction column through the open lower end of the column, and optionally for discharging (i.e., expelling) fluid out through the open lower end of the column. Thus, it is a feature certain embodiments of the present invention that fluid enters and exits the extraction column through the same open end of the column, typically the open lower end. This is in contradistinction with the operation of some extraction columns, where fluid enters the column through one open end and exits through the other end after traveling through an extraction media, i.e., similar to conventional column chromatography. The fluid can be a liquid, such as a sample solution, wash solution or desorption solvent. The fluid can also be a gas, e.g., air used to blow liquid out of the extraction column.

In other embodiments of the present invention, fluid enters the column through one end and exits through the other. In some embodiments, the invention provides extraction methods that involve a hybrid approach; that is, one or more fluids enter the column through one end and exit through the other, and one more fluids enter and exit the column through the same open end of the column, e.g., the lower end. Thus, for example, in some methods the sample solution and/or wash solution are introduced through the top of the column and exit through the bottom end, while the desorption solution enters and exits through the bottom opening of the column. Aspiration and discharge of solution through the same end of the column can be particularly advantageous in procedures designed to minimize sample loss, particularly when small volumes of liquid are used. A good example would be a procedure that employs a very small volume of desorption solvent, e.g., a procedure involving a high enrichment factor.

The column body can be can be composed of any material that is sufficiently non-porous that it can retain fluid and that is compatible with the solutions, media, pumps and analytes used. A material should be employed that does not substantially react with substances it will contact during use of the extraction column, e.g., the sample solutions, the analyte of interest, the extraction media and desorption solvent. A wide range of suitable materials are available and known to one of skill in the art, and the choice is one of design. Various plastics make ideal column body materials, but other materials such as glass, ceramics or metals could be used in some embodiments of the invention. Some examples of preferred materials include polysulfone, polypropylene, polyethylene, polyethyleneterephthalate, polyethersulfone, polytetrafluoroethylene, cellulose acetate, cellulose acetate butyrate, acrylonitrile PVC copolymer, polystyrene, polystyrene/acrylonitrile copolymer, polyvinylidene fluoride, glass, metal, silica, and combinations of the above listed materials.

Some specific examples of suitable column bodies are provided in the Examples.

Extraction Media

The extraction media used in the column is preferably a form of water-insoluble particle (e.g., a porous or non-porous bead) that has an affinity for an analyte of interest. Typically, the analyte of interest is a protein, peptide or nucleic acid. The extraction processes can be affinity, reverse phase, normal phase, ion exchange, hydrophobic interaction chromatography, or hydrophilic interaction chromatography agents or any media that use buffers, solvents, and/or chaotropic reagents to separate or purify DNA vectors. In general, the term "extraction media" is used in a broad sense to encompass any media capable of effecting separation, either partial or complete, of an analyte from another. Thus, the terms "separation column" and "extraction column" can be used interchangeably.

The bed volume of the extraction media used in the extraction columns of the invention is typically small, typically in the range of 5-1000 µL, preferably in the range of 5-100 µL.

The low bed volumes employed in certain embodiments allow for the use of relatively small amounts of extraction media. For example, some embodiments of the invention employ a bed of extraction media having a dry weight of less than 1 gram Many of the extraction media types suitable for use in the invention are selected from a variety of classes of chromatography media. It has been found that many of these chromatography media types and the associated chemistries are suited for use as solid phase extraction media in the devices and methods of this invention.

Thus, examples of suitable extraction media include resin beads used for extraction and/or chromatography. Preferred resins include gel resins, pellicular resins, and macroporous resins.

The term "gel resin" refers to a resin comprising low-crosslinked bead materials that can swell in a solvent, e.g., upon hydration. Crosslinking refers to the physical linking of the polymer chains that form the beads. The physical linking is normally accomplished through a crosslinking monomer that contains bi-polymerizing functionality so that during the polymerization process, the molecule can be incorporated into two different polymer chains. The degree of crosslinking for a particular material can range from 0.1 to 30%, with 0.5 to 10% normally used. 1 to 5% crosslinking is most common. A lower degree of crosslinking renders the bead more permeable to solvent, thus making the functional sites within the bead more accessible to analyte.

The term "pellicular resins" refers to materials in which the functional groups are on the surface of the bead or in a thin layer on the surface of the bead. In some embodiments, the surface of the particle is the functional surface. The interior of the bead is solid, usually highly crosslinked, and usually inaccessible to the solvent and analytes. Pellicular resins generally have lower capacities than gel and macroporous resins.

The term "macroporous resin" refers to highly crosslinked resins having high surface area due to a physical porous structure that formed during the polymerization process. Generally an inert material (such as a solid or a liquid that does not solvate the polymer that is formed) is polymerized with the bead and then later washed out, leaving a porous structure. Crosslinking of macroporous materials range from 5% to 90% with perhaps a 25 to 55% crosslinking the most common materials. Macroporous resins behave similar to pellicular resins except that in effect much more surface area is available for interaction of analyte with resin functional groups.

Examples of resins beads include polystyrene/divinylbenzene copolymers, poly methylmethacrylate, protein G beads (e.g., for IgG protein purification), MEP Hypercel™ beads (e.g., for IgG protein purification), affinity phase beads (e.g., for protein purification), ion exchange phase beads (e.g., for protein purification), hydrophobic interaction beads (e.g., for protein purification), reverse phase beads (e.g., for nucleic acid or protein purification), and beads having an affinity for molecules analyzed by label-free detection. Silica beads are also suitable.

Soft gel resin beads, such as agarose and sepharose based beads, are found to work surprisingly well in columns and methods of this invention. In conventional chromatography fast flow rates can result in bead compression, which results in increased back pressure and adversely impacts the ability to use these gels with faster flow rates. In the present invention, relatively small bed volumes are used, and it appears that this allows for the use of high flow rates with a minimal amount of bead compression and the problem attendant with such compression.

The average particle diameters of beads of the invention are typically in the range of about 20 μm to several millimeters, e.g., diameters in ranges having lower limits of 20 μm, 30 μm, 40 μm, 50 μm, 60 μm, 70 μm, 80 μm, 90 μm, 100 μm, 150 μm, 200 μm, 300 μm, or 500 μm, and upper limits of 10 μm, 20 μm, 30 μm, 40 μm, 50 μm, 60 μm, 70 μm, 80 μm, 90 μm, 100 μm, 150 μm, 200 μm, 300 μm, 500 μm, 750 μm, 1 mm, 2 mm, or 3 mm.

The extraction chemistry employed in the present invention can take any of a wide variety of forms. For example, the extraction media can be selected from, or based on, any of the extraction chemistries used in solid-phase extraction and/or chromatography, e.g., reverse-phase, normal phase, hydrophobic interaction, hydrophilic interaction, ion-exchange, thiophilic separation, hydrophobic charge induction or affinity binding. Because the invention is particularly suited to the purification and/or concentration of DNA vectors, extraction surfaces capable of adsorbing such molecules are particularly relevant. See, e.g., SEPARATION AND SCIENCE TECHNOLOGY Vol. 2:HANDBOOK OF BIOSEPARATIONS, edited by Satinder Ahuja, Academic Press (2000).

Affinity extractions use a technique in which a bio-specific adsorbent is prepared by coupling a specific ligand (such as an enzyme, antigen, or hormone) for the analyte, (e.g., macromolecule) of interest to a solid support. This immobilized ligand will interact selectively with molecules that can bind to it. Molecules that will not bind elute un-retained. The interaction is selective and reversible. The references listed below show examples of the types of affinity groups that can be employed in the practice of this invention are hereby incorporated by reference herein in their entireties. Antibody Purification Handbook, *Amersham Biosciences*, Edition AB, 18-1037-46 (2002); Protein Purification Handbook, *Amersham Biosciences*, Edition AC, 18-1132-29 (2001); Affinity Chromatography Principles and Methods, *Amersham Pharmacia Biotech*, Edition AC, 18-1022-29 (2001); The Recombinant Protein Handbook, *Amersham Pharmacia Biotech*, Edition AB, 18-1142-75 (2002); and *Protein Purification: Principles, High Resolution Methods, and Applications*, Jan-Christen Janson (Editor), Lars G. Ryden (Editor), Wiley, John & Sons, Incorporated (1989). Examples of suitable resin binding agents are affinity interactions, nucleic acid—nucleic acid interaction, protein antibody interactions and other groups that have specific chemical interactions with nucleic acids.

In other embodiments of the invention, extraction surfaces are employed that are generally less specific than the affinity binding agents discussed above. These extraction chemistries are still often quite useful. Examples include ion exchange, reversed phase, normal phase, chaotrophic normal phase, hydrophobic interaction and hydrophilic interaction extraction or chromatography surfaces. In general, these extraction chemistries, methods of their use, appropriate solvents, etc. are well known in the art, and in particular are described in more detail in U.S. patent application Ser. Nos. 10/434,713 and 10/620,155, and references cited therein, e.g., Chromatography, $5^{th}$ edition, PART A: FUNDAMENTALS AND TECHNIQUES, editor: E. Heftmann, Elsevier Science Publishing Company, New York, pp A25 (1992); ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); CHROMATOGRAPHY TODAY, Colin F. Poole and Salwa K. Poole, and Elsevier Science Publishing Company, New York, pp 3 94 (1991); and ORGANIC SYNTHESIS ON SOLID PHASE, F. Dorwald Wiley VCH Verlag Gmbh, Weinheim 2002.

Frits

In some embodiments of the invention, one or more frits is used to contain the bed of extraction in, for example, a column. Frits can take a variety of forms, and can be constructed from a variety of materials, e.g., polymer, glass, ceramic, metal, fiber. The frits of the invention are porous, since it is necessary for fluid to be able to pass through the frit. The frit should have sufficient structural strength so that frit integrity can contain the extraction media in the column. It is desirable that the frit have little or no affinity for chemicals with which it will come into contact during the extraction process, particularly the DNA vector of interest. Thus in many embodiments of the invention, it desirable to use a frit that has a minimal tendency to bind or otherwise interact with DNA vectors.

Frits of various pores sizes and pore densities may be used provided the free flow of liquid is possible and the beads are held in place within the extraction media bed. Frits of pore size large enough to prevent plugging of cell debris are of particular interest.

In one embodiment, one frit (e.g., a lower, or bottom, frit) is bonded to and extends across the open channel of the column body. Preferably, the bottom frit is attached at or near the open lower end of the column, e.g., bonded to and extend across the open lower end. Normally, a bed of separation media, such as an extraction media, is positioned inside the open channel and in contact with the bottom frit.

In certain embodiments, an optional top frit may be employed. For example, in some embodiments, a second frit is bonded to and extends across the open channel between the bottom frit and the open upper end of the column body. In this embodiment, the top frit, bottom frit and column body (i.e., the inner surface of the channel) define an extraction media chamber wherein a bed of extraction media is positioned. The frits should be securely attached to the column body and extend across the opening and/or open end so as to completely occlude the channel, thereby substantially confining the bed of extraction media inside the extraction media chamber. In some preferred embodiments of the invention, the bed of extraction media occupies at least 50% of the volume of the extraction media chamber, more preferably 80%, 90%, 95%, or substantially 100% of the volume. In some embodiments, the invention the space between the extraction media bed and the upper and lower frits is negligible, i.e., the frits are in substantial contact with upper and lower surfaces of the extraction media bed, holding a well-packed bed of extraction media securely in place.

In some preferred embodiments of the invention, the bottom frit is located at the open lower end of the column body. This configuration is shown in the figures and exemplified in the Examples, but is not required, i.e., in some embodiments, the bottom frit is located at some distance up the column body from the open lower end. However, in view of the advantage the come with minimizing dead volume in the column, it is desirable that the lower frit and extraction media chamber be located at or near the lower end. In some cases, this can mean that the bottom frit is attached to the face of the open lower end. However, in some cases there can be some portion of the lower end extending beyond the bottom frit. For the purposes of this invention, so long as the length of this extension is such that it does not substantially introduce dead volume into the extraction column or otherwise adversely impact the function of the column, the bottom frit is considered to be located at the lower end of the column body. In some embodiments of the invention, the volume defined by the bottom frit, channel surface, and the face of the open lower end (i.e., the channel volume below the bottom frit) is less than the volume of the extraction media chamber, or less than 10% of the volume of the extraction media chamber, or less than 1% of the volume of the extraction media chamber.

In some embodiments of the invention, the extraction media chamber is positioned near one end of the column, which for purposes of explanation will be described as the bottom end of the column. The area of the column body channel above the extraction media chamber can be quite large in relation to the size of the extraction media chamber. For example, in some embodiments the volume of the extraction chamber is equal to less than 50%, less than 20%, less than 10%, less than 5%, less than 2%, less than 1% or less than 0.5% of the total internal volume of the column body. In operation, solvent can flow through the open lower end of the column, through the bed of extraction media and out of the extraction media chamber into the section of the channel above the chamber. For example, when the column body is a pipette tip, the open upper end can be fitted to a pipettor and a solution drawn through the extraction media and into the upper part of the channel.

Some embodiments of the invention employ large pore size frit. Frits of the invention preferably have pore openings or mesh openings of a size in the range of about 5-500 µm, more preferably 10-200 µm, and still more preferably 100-150 µm, e.g., about 120 µm. The performance of the column is typically enhanced by the use of frits having pore or mesh openings sufficiently large so as to minimize the plugging from unclarified cell debris and biological particulates. Both 50 um and 70 um pore size frits are acceptable provided the frit diameter is 1 mm or greater. For columns of larger diameter, frit pore size of 20, 33, 37 and 43 um pore size are acceptable. The particle space between the resin is important also. The space can increase with a looser packing of the column. A frit pore size of 100 um was used with a range of different resins types and column frit diameters.

The use of membrane screens as described herein typically provide this low resistance to flow and hence better flow rates, reduced back pressure and minimal distortion of the bed of extraction media. The pore or mesh openings of course should not be so large that they are unable to adequately contain the extraction media in the chamber.

Some embodiments of the invention employ a thin frit, preferably less than 1000 µm in thickness (e.g., in the range of 20-1000 µm, 40-350 µm, or 50-350 µm), more preferably less than 200 µm in thickness (e.g., in the range of 20-200 µm, 40-200 µm, or 50-200 µm), more preferably less than 100 µm in thickness (e.g., in the range of 20-100 µm, 40-100 µm, or 50-100 µm). However, thicker frits, up to several mm, 5 and even 10 mm, thick may be used if the pore size of the frit can be increased dramatically. Increasing the frit thickness can only be done if the particle size of the packing can be increased. The practical limit of the particle size depends on capacity of the bead. This can be done only with particles that do not fall through the frit.

Some preferred embodiments of the invention employ a membrane screen as the frit. The membrane screen should be strong enough to not only contain the extraction media in the column bed, but also to avoid becoming detached or punctured during the actual packing of the media into the column bed. Membranes can be fragile, and in some embodiments must be contained in a framework to maintain their integrity during use. However, it is desirable to use a membrane of sufficient strength such that it can be used without reliance on such a framework.

The membrane can be a woven or non-woven mesh of fibers that may be a mesh weave, a random orientated mat of fibers i.e. a "polymer paper," a spun bonded mesh, an etched or "pore drilled" paper or membrane such as nuclear track etched membrane or an electrolytic mesh (see, e.g., U.S. Pat. No. 5,556,598). The membrane may be, e.g., polymer, glass, or metal provided the membrane is low dead volume, allows movement of the various sample and processing liquids through the column bed, may be attached to the column body, is strong enough to withstand the bed packing process, is strong enough to hold the column bed of beads, and does not interfere with the extraction process i.e. does not adsorb or denature the sample molecules.

The frit can be attached to the column body by any means which results in a stable attachment. For example, the screen can be bonded to the column body through welding or gluing. Gluing can be done with any suitable glue, e.g., silicone, cyanoacrylate glue, epoxy glue, and the like. The glue or weld joint must have the strength required to withstand the process of packing the bed of extraction media and to contain the extraction media with the chamber. For glue joints, a glue should be selected employed that does not adsorb or denature the sample molecules.

For example, glue can be used to attach a membrane to the tip of a pipette tip-based extraction column, i.e., a column wherein the column body is a pipette tip. A suitable glue is applied to the end of the tip. In some cases, a rod may be inserted into the tip to prevent the glue from spreading beyond the face of the body. After the glue is applied, the tip is brought into contact with the membrane frit, thereby attaching the membrane to the tip. After attachment, the tip and membrane may be brought down against a hard flat surface and rubbed in a circular motion to ensure complete attachment of the membrane to the column body. After drying, the excess membrane may be trimmed from the column with a razor blade.

Alternatively, the column body can be welded to the membrane by melting the body into the membrane, or melting the membrane into the body, or both. In one method, a membrane is chosen such that its melting temperature is higher than the melting temperature of the body. The membrane is placed on a surface, and the body is brought down to the membrane and heated, whereby the face of the body will melt and weld the membrane to the body. The body may be heated by any of a variety of means, e.g., with a hot flat surface, hot air or ultrasonically. Immediately after welding, the weld may be cooled with air or other gas to improve the likelihood that the weld does not break apart.

Alternatively, a frit can be attached by means of an annular pip, as described in U.S. Pat. No. 5,833,927. This mode of attachment is particularly suited to embodiment where the frit is a membrane screen.

The frits of the invention, e.g., a membrane screen, can be made from any material that has the required physical properties as described herein. Examples of suitable materials include nylon, polyester, polyamide, polycarbonate, cellulose, polyethylene, nitrocellulose, cellulose acetate, polyvinylidine difluoride, polytetrafluoroethylene (PTFE), polypropylene, polysulfone, PEEK, PVC, metal and glass. A specific example of a membrane screen is the 43 µm pore size Spectra/Mesh® polyester mesh material which is available from Spectrum Labs (Ranch Dominguez, Calif., PN 145837).

Pore size characteristics of membrane filters can be determined, for example, by use of method #F316-30, published by ASTM International, entitled "Standard Test Methods for Pore Size Characteristics of Membrane Filters by Bubble Point and Mean Flow Pore Test."

In certain embodiments of the invention, a wad of fibrous material is included in the device, which extends across the open channel below the open upper end of the column body, wherein the wad of fibrous material and open channel define a media chamber, wherein the bed of extraction media is positioned within the media chamber. In some embodiments, the wad of fibrous material is used in lieu of an upper frit.

Extraction Column Assembly

The extraction columns of the invention can be constructed by a variety of methods using the teaching supplied herein. In some preferred embodiments, the extraction column can be constructed by the engagement (i.e., attachment) of upper and lower tubular members (i.e., column bodies) that combine to form the extraction column. Examples of this mode of column construction are described in the Examples and depicted in the figures.

In some preferred embodiments of the invention, an extraction column is constructed by the engaging outer and inner column bodies, where each column body has two open ends (e.g., an open upper end and an open lower end) and an open channel connecting the two open ends (e.g., a tubular body, such as a pipette tip). The outer column body has a first frit (preferably a membrane frit) bonded to and extending across the open lower end, either at the very tip of the open end or near the open end. The section of the open channel between the open upper end and the first frit defines an outer column body. The inner column body likewise has a frit (preferably a membrane frit) bonded to and extending across its open lower end.

To construct a column according to this embodiment, an extraction media of interest is disposed within the lower column body, e.g., by orienting the lower column body such that the open lower end is down and filling or partially filling the open channel with the resin, e.g., in the form of a slurry. The inner column body, or at least some portion of the inner column body, is then inserted into the outer column body such that the open lower end of the inner body (where second frit is attached) enters the outer column body first. The inner column body is sealingly positioned within the open channel of the outer column body, i.e., the outer surface of the inner column body forms a seal with the surface of the open. The section of the open channel between the first and second frits contains the extraction media, and this space defines a media chamber. In general, it is advantageous that the volume of the media chamber (and the volume of the bed of extraction media positioned with said media chamber) is less than the outer column body, since this difference in volume facilitates the introduction of extraction media into the outer column body and hence simplifies the production process. This is particularly advantageous in embodiments of the invention wherein the extraction columns are mass produced.

In certain embodiments of the above manufacturing process, the inner column body is stably affixed to the outer column body by frictional engagement with the surface of the open channel.

Figure 2:
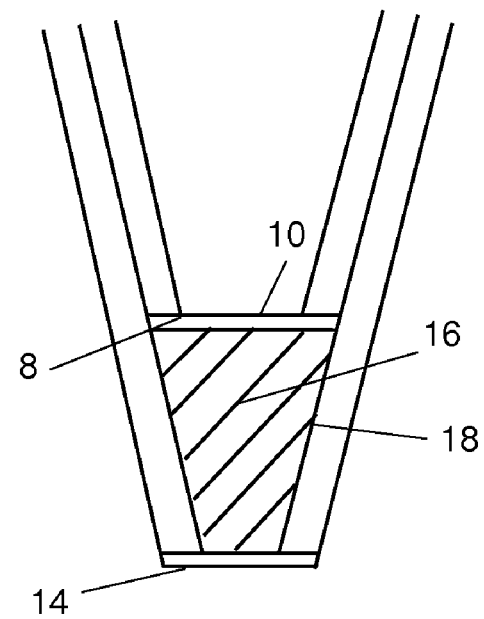
FIG. 2 is an enlarged view of the extraction column of FIG. 1.

In some embodiments, one or both of the column bodies are tubular members, particularly pipette tips, sections of pipette tips or modified forms of pipette tips. For example, an embodiment of the invention wherein in the two tubular members are sections of pipette tips is depicted in FIG. 1 (FIG. 2 is an enlarged view of the open lower end and extraction media chamber of the column). This embodiment is constructed from a frustoconical upper tubular member 2 and a frustoconical lower tubular member 3 engaged therewith. The engaging end 6 of the lower tubular member has a tapered bore that matches the tapered external surfaced of the engaging end 4 of the upper tubular member, the engaging end of the lower tubular member receiving the engaging end of the upper tubular member in a telescoping relation. The tapered bore engages the tapered external surface snugly so as to form a good seal in the assembled column.

A membrane screen 10 is bonded to and extends across the tip of the engaging end of the upper tubular member and constitutes the upper frit of the extraction column. Another membrane screen 14 is bonded to and extends across the tip of the lower tubular member and constitutes the lower frit of the extraction column. The extraction media chamber 16 is defined by the membrane screens 10 and 14 and the channel surface 18, and is packed with extraction media.

The pore volume of the membrane screens 10 and 14 is low to minimize the dead volume of the column. The sample and desorption solution can pass directly from the vial or reservoir into the bed of extraction media. The low dead volume permits desorption of the analyte into the smallest possible desorption volume, thereby maximizing analyte concentration.

The volume of the extraction media chamber 16 is variable and can be adjusted by changing the depth to which the upper tubular member engaging end extends into the lower tubular member, as determined by the relative dimensions of the tapered bore and tapered external surface.

The sealing of the upper tubular member to the lower tubular in this embodiment is achieved by the friction of a press fit, but could alternatively be achieved by welding, gluing or similar sealing methods.

Note that in this and similar embodiments, a portion of the inner column body (in this case, a majority of the pipette tip 2) is not disposed within the first channel, but instead extends out of the outer column body. In this case, the open upper end of the inner column body is adapted for operable attachment to a pump, e.g., a pipettor.

Figure 3:
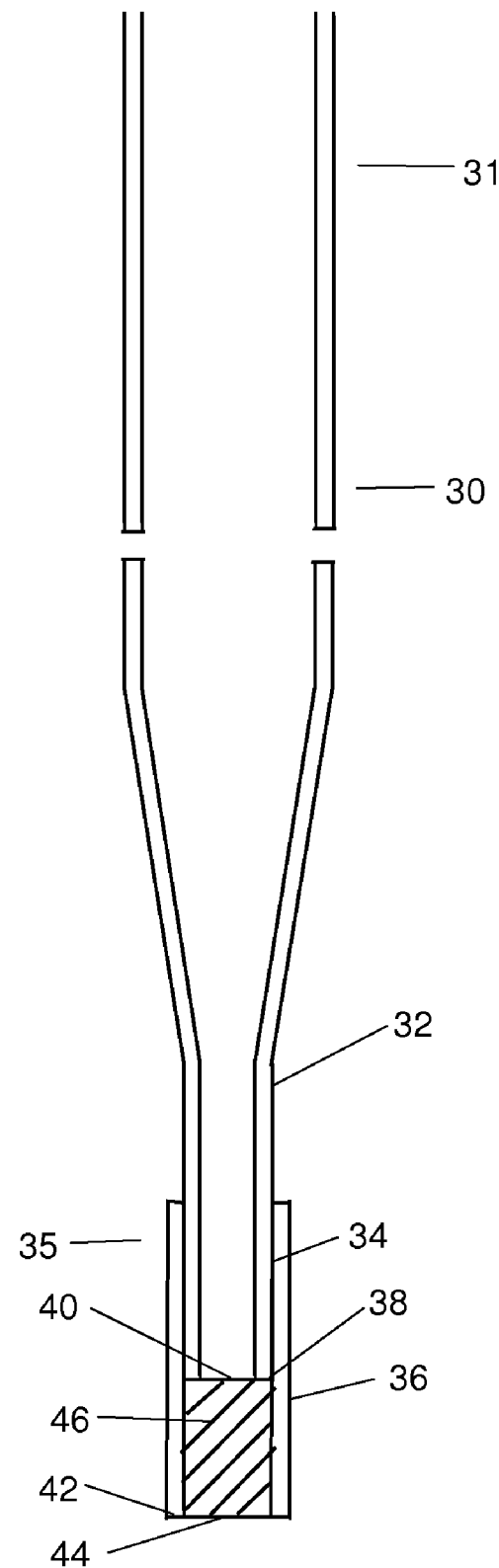
FIG. 3 depicts an embodiment of the invention where the extraction column is constructed from two cylindrical members.

FIG. 3 depicts an embodiment of the invention comprising an upper and lower tubular member engaged in a telescoping relation that does not rely on a tapered fit. Instead, in this embodiment the engaging ends 34 and 35 are cylindrical, with the outside diameter of 34 matching the inside diameter of 35, so that the concentric engaging end form a snug fit. The engaging ends are sealed through a press fit, welding, gluing or similar sealing methods. The volume of the extraction bed can be varied by changing how far the length of the engaging end 34 extends into engaging end 35. Note that the diameter of the upper tubular member 30 is variable, in this case it is wider at the upper open end 31 and tapers down to the narrower engaging end 34. This design allows for a larger volume in the column channel above the extraction media, thereby facilitating the processing of larger sample volumes and wash volumes. The size and shape of the upper open end can be adapted to conform to a pump used in connection with the column. For example, upper open end 31 can be tapered outward to form a better friction fit with a pump such as a pipettor or syringe.

A membrane screen 40 is bonded to and extends across the tip 38 of engaging end 34 and constitutes the upper frit of the extraction column. Another membrane screen 44 is bonded to and extends across the tip 42 of the lower tubular member 36 and constitutes the lower frit of the extraction column. The extraction media chamber 46 is defined by the membrane screens 40 and 44 and the open interior channel of lower tubular member 36, and is packed with extraction media.

Figure 4:
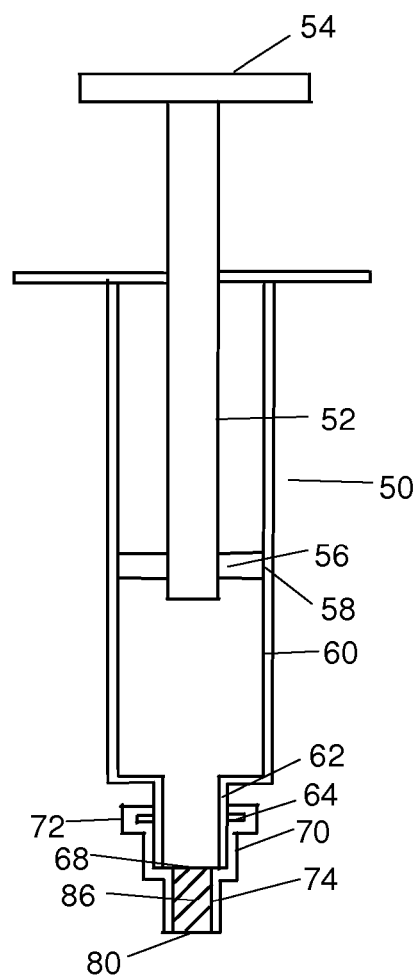
FIG. 4 depicts a syringe pump embodiment of the invention with a cylindrical bed of solid phase media in the tip.
Figure 5:
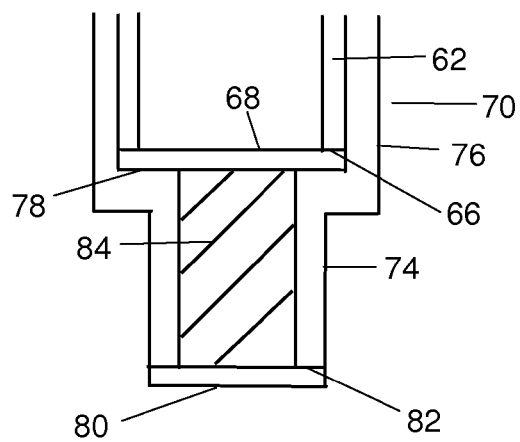
FIG. 5 depicts an enlarged view of the extraction column element of the syringe pump embodiment of FIG. 4.

FIG. 4 is a syringe pump embodiment of the invention with a cylindrical bed of extraction media in the tip, and FIG. 5 is an enlargement of the top of the syringe pump embodiment of FIG. 4. These figures show a low dead volume column based on using a disposable syringe and column body. Instead of a pipettor, a disposable syringe is used to pump and contain the sample.

The upper portion of this embodiment constitutes a syringe pump with a barrel 50 into which a plunger 52 is positioned for movement along the central axis of the barrel. A manual actuator tab 54 is secured to the top of the plunger 52. A concentric sealing ring 56 is secured to the lower end of the plunger 52. The outer surface 58 of the concentric sealing ring 56 forms a sealing engagement with the inner surface 60 of the barrel 50 so that movement of the plunger 52 and sealing ring 56 up or down in the barrel moves liquid up or down the barrel.

The lower end of the barrel 50 is connected to an inner cylinder 62 having a projection 64 for engaging a Luer adapter. The bottom edge 66 of the inner cylinder 62 has a membrane screen 68 secured thereto. The inner cylinder 62 slides in an outer sleeve 70 with a conventional Luer adaptor 72 at its upper end. The lower segment 74 of the outer sleeve 70 has a diameter smaller than the upper portion 76, outer sleeve 70 forming a ledge 78 positioned for abutment with the lower end 66 and membrane screen 68. A membrane screen 80 is secured to the lower end 82 of the lower segment 74. The extraction media chamber 84 is defined by the upper and lower membrane screens 68 and 80 and the inner channel surface of the lower segment 74. The extraction beads are positioned in the extraction media chamber 84. The volume of extraction media chamber 84 can be adjusted by changing the length of the lower segment 74.

In other embodiments of this general method of column manufacture, the entire inner column body is disposed within the first open channel. In these embodiments, the first open upper end is normally adapted for operable attachment to a pump, e.g., the outer column body is a pipette tip and the pump is a pipettor. In some preferred embodiments, the outer diameter of the inner column body tapers towards its open lower end, and the open channel of the outer column body is tapered in the region where the inner column body frictionally engages the open channel, the tapers of the inner column body and open channel being complementary to one another. This complementarity of taper permits the two bodies to fit snuggly together and form a sealing attachment, such that the resulting column comprises a single open channel containing the bed of extraction media bounded by the two frits.

Figure 6:
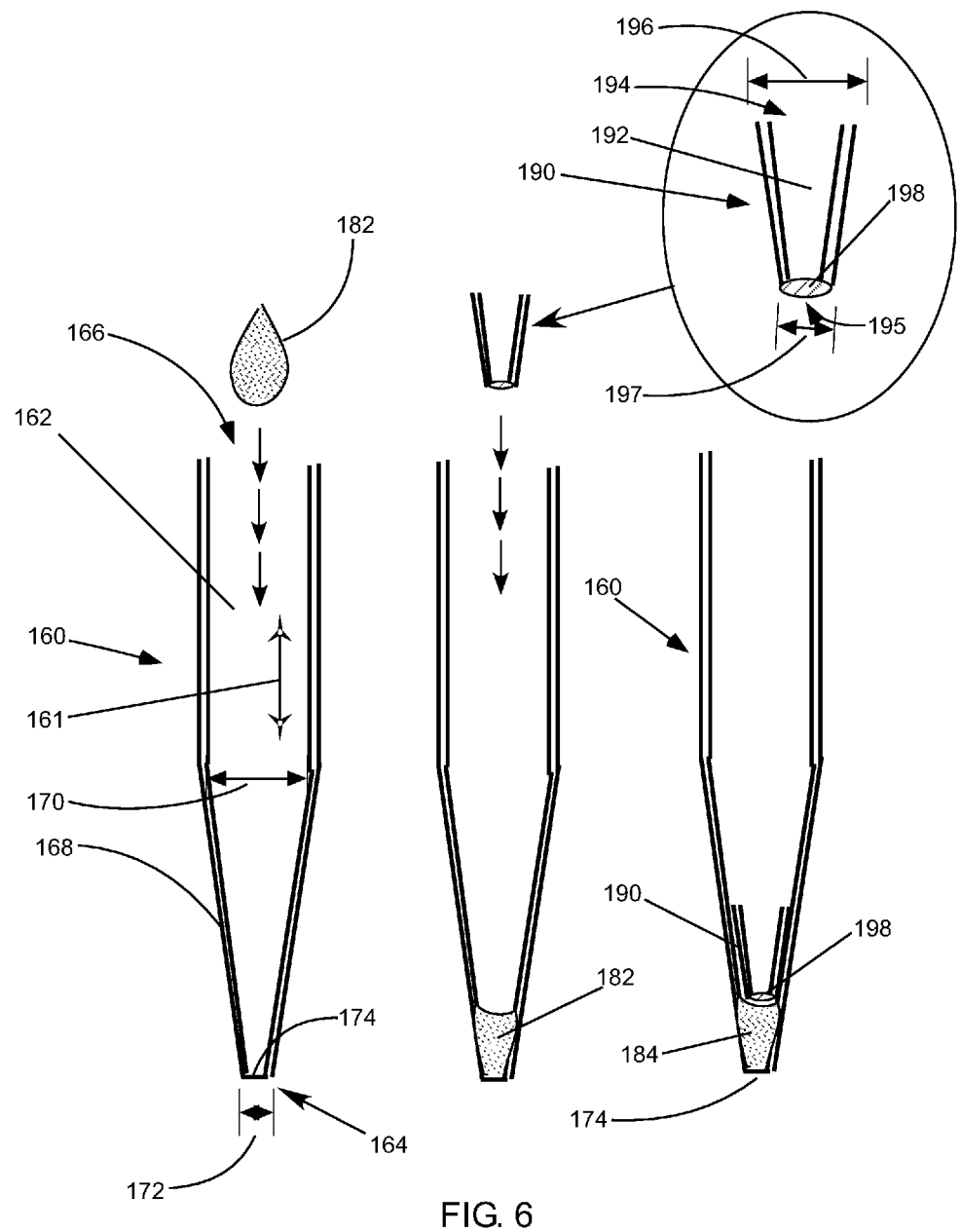
FIG. 6 depicts preferred embodiments of the invention.

FIG. 6 illustrates the construction of an example of this embodiment of the extraction columns of the invention. This example includes an outer column body 160 having a longitudinal axis 161, a central through passageway 162 (i.e., an open channel), an open lower end 164 for the uptake and/or expulsion of fluid, and an open upper end 166 for operable attachment to a pump, e.g., the open upper end is in communication with a pipettor or multi-channel pipettor. The communication can be direct or indirect, e.g., through one or more fittings, couplings or the like, so long as operation of the pump effects the pressure in the central through passageway (referred to elsewhere herein as the "head space"). The outer column body includes a frustoconical section 168 of the through passageway 162, which is adjacent to the open lower end 164. The inner diameter of the frustoconical section decreases from a first inner diameter 170, at a position in the frustoconical section distal to the open lower end, to a second inner diameter 172 at the open lower end. A lower frit 174, preferably a membrane screen, is bonded to and extends across the open lower end 164. In a preferred embodiment a membrane frit can be bound to the outer column body by methods described herein, such as by gluing or welding. This embodiment further includes a ring 176 having an outer diameter 178 that is less than the first inner diameter 170 and greater than the second inner diameter 174. An optional upper frit 198, preferably a membrane screen, is bonded to and extends across the ring. The upper frit may be place near the top of the top of the resin bed or may be positioned substantially above the top of the resin bed.

To construct the column, a desired quantity of extraction media 182, preferably in the form of a slurry, is introduced into the through passageway through the open upper end and positioned in the frustoconical section adjacent to the open lower end. The extraction media preferably forms a packed bed in contact with the lower frit 174. The optional upper frit, lower frit, and the surface of the through passageway bounded by the upper and lower frits define an extraction media chamber 184. The amount of extraction media introduced into the column is normally selected such that the resulting packed bed substantially fills the extraction media chamber, preferably making contact with the upper and lower frits.

The upper frit can take any of a number of geometries so long as the frit is shaped to conform with the internal geometry of the frustoconical section and includes a through passageway through which solution can pass. FIG. 6 depicts a preferred embodiment of the upper frit in the form of a frustoconical member 190 having a central through passageway 192 connecting an open upper end 194 and open lower end 195. The outer diameter of the frustoconical member decreases from a first outer diameter 196 at the open upper end to a second outer diameter 197 at the open lower end. The second outer diameter 197 is greater than the second inner diameter 172 and less than the first inner diameter 170. The first outer diameter 196 is less than or substantially equal to the first inner diameter 170. An upper frit 198 is bonded to and extends across the open lower end 195. The frustoconical member 190 is introduced into the through passageway of an outer column body containing a bed of extraction media positioned at the lower frit 174. The tapered outer surface of the frustoconical member matches and the taper of the frustoconical section of the open passageway, and the two surfaces make a sealing contact. The extended frustoconical configuration of this embodiment of the ring facilitates the proper alignment and seating of the ring in the outer passageway.

Because of the friction fitting of the ring to the surface of the central through passageway, it is normally not necessary to use additional means to bond the upper frit to the column. If desired, one could use additional means of attachment, e.g., by bonding, gluing, welding, etc. In some embodiments, the inner surface of the frustoconical section and/or the ring is modified to improve the connection between the two elements, e.g., by including grooves, locking mechanisms, etc.

In the foregoing embodiments, the ring and latitudinal cross sections of the frustoconical section are illustrated as circular in geometry. Alternatively, other geometries could be employed, e.g., oval, polygonal or otherwise. Whatever the geometries, the ring and frustoconical shapes should match to the extent required to achieve and adequately sealing engagement. The frits are preferably, bit not necessarily, positioned in a parallel orientation with respect to one another and perpendicular to the longitudinal axis.

Other embodiments of the invention exemplifying different methods of construction are also described in the examples.

Pump

In some modes of using the extraction columns of the invention, a pump is attached to the upper open end of the column and used to aspirated and discharge the sample from the column. The pump can take any of a variety of forms, so long as it is capable of generating a negative internal column pressure to aspirate a fluid into the column channel through the open lower end. In some preferred embodiments of the invention the pump is also able to generate a positive internal column pressure to discharge fluid out of the open lower end. Alternatively, other methods can be used for discharging solution from the column, e.g., centrifugation.

The pump should be capable of pumping liquid or gas, and should be sufficiently strong so as to be able to draw a desired sample solution, wash solution and/or desorption solvent through the bed of extraction media. In order to evacuate liquids from the packed bed and introduce a gas such as air, it is desirable that the pump be able to blow or pull air through the column. A pump capable of generating a strong pressure will be able to more effectively blow gas through the column, driving liquid out of the interstitial volume and contributing to a more highly purified, concentrated analyte.

In some preferred embodiments of the invention, the pump is capable of controlling the volume of fluid aspirated and/or discharged from the column, e.g., a pipettor. This allows for the metered intake and outtake of solvents, which facilitates more precise elution volumes to maximize sample recovery and concentration.

Non-limiting examples of suitable pumps include a pipettor, syringe, peristaltic pump, pressurized container, or centrifugal pump. Preferred pumps have good precision, good accuracy and minimal hysteresis, can manipulate small volumes, and can be directly or indirectly controlled by a computer or other automated means, such that the pump can be used to aspirate, infuse and/or manipulate a predetermined volume of liquid. The required accuracy and precision of fluid manipulation will vary depending on the step in the extraction procedure, the enrichment of the biomolecule desired, and the dimensions of the extraction column and bed volume.

The sample solution enters the column through one end, and passes through the extraction bed or some portion of the entire length of the extraction bed, eventually exiting the channel through either the same end of the column or out the other end. Introduction of the sample solution into the column can be accomplished by any of a number of techniques for driving or drawing liquid through a channel. Examples would include use of a pump (as described above) gravity, centrifugal force, capillary action, or gas pressure to move fluid through the column. The sample solution is preferably moved through the extraction bed at a flow rate that allows for adequate contact time between the sample and extraction surface. The sample solution can be passed through the bed more than one time, either by circulating the solution through the column in the same direction two or more times, or by passing the sample back and forth through the column two or more times (e.g., by oscillating a plug or series of plugs of desorption solution through the bed). In some embodiments, it is important that the pump be able to pump air, thus allowing for liquid to be blown out of the bed. Preferred pumps have good precision, good accuracy and minimal hysteresis, can manipulate small volumes, and can be directly or indirectly controlled by a computer or other automated means, such that the pump can be used to aspirate, infuse and/or manipulate a predetermined volume of liquid. The required accuracy and precision of fluid manipulation in the column will vary depending on the step in the extraction procedure, the enrichment of the biomolecule desired, and the dimensions of the column.

Solvents

Extractions of the invention typically involve the loading of the DNA vector in a sample solution, an optional wash with a rinse solution, and elution of the analyte into a desorption solution. The nature of these solutions will now be described in greater detail.

With regard to the sample solution, it typically consists of the DNA vector dissolved in a solvent in which the analyte is soluble, and in which the DNA vector will bind to the extraction surface. Preferably, the binding is strong, resulting in the binding of a substantial portion of the analyte, and optimally substantially all of the analyte will be bound under the loading protocol used in the procedure. The solvent should also be gentle, so that the native structure and function of the analyte is retained upon desorption from the extraction surface. Examples of sample solutions include cells lysates, hybridoma growth medium, cell-free translation or transcription reaction mixtures, extracts from tissues, organs, or biological samples, and extracts derived from biological fluids.

It is important that the sample solvent not only solubilize the DNA vector, but also that it is compatible with binding to the extraction phase. For example, where the extraction phase is based on ion exchange, the ionic strength of the sample solution should be buffered to an appropriate pH such that the charge of the analyte is opposite that of the immobilized ion, and the ionic strength should be relatively low to promote the ionic interaction. In the case of a normal phase extraction, the sample loading solvent should be chaotropic reagent or the like. Depending upon the nature of the sample and extraction process, other constituents might be beneficial, e.g., reducing agents, detergents, stabilizers, denaturants, chelators, metals, enzymes etc.

A wash solution, if used, should be selected such that it will remove non-desired contaminants with minimal loss or damage to the bound analyte. The properties of the wash solution are typically intermediate between that of the sample and desorption solutions.

The desorption solvent and buffer should be just strong enough to quantitatively desorb the analyte while leaving strongly bound interfering materials behind. The solvents and buffer are chosen to be compatible with the analyte and the ultimate use.

Examples of suitable phases for solid phase extraction and desorption solvents are shown in Tables C and D.

TABLE C

|  | Normal Phase Extraction | Normal Phase Chaotropic Extraction | Reverse Phase Ion-Pair Extraction |
|---|---|---|---|
| Typical solvent polarity range | Low to medium | High to medium | High to medium |
| Typical sample loading solvent | Hexane, toluene, $CH_2Cl_2$ | chaotropic buffers alcohol | $H_2O$, buffers, ion-pairing reagent |

TABLE C-continued

|  | Normal Phase Extraction | Normal Phase Chaotropic Extraction | Reverse Phase Ion-Pair Extraction |
|---|---|---|---|
| Typical desorption solvent | Ethyl acetate, acetone, CH₃CN (Acetone, acetonitrile, isopropanol, methanol, water, buffers) | H₂O/buffer | H₂O/CH₃OH, ion-pairing reagent H₂O/CH₃CN, ion-pairing reagent (Methanol, chloroform, acidic methanol, basic methanol, tetrahydrofuran, acetonitrile, acetone, ethyl acetate) |
| Sample elution selectivity | Least polar sample components first | Most polar sample components first | Most polar sample components first |
| Solvent change required to desorb | Increase solvent polarity | Decrease chaotropic buffer | Decrease solvent polarity |

TABLE D

| Desorption Solvent Features | Ion Exchange Extraction | Hydrophobic Interaction Extraction | Affinity Phase Extraction |
|---|---|---|---|
| Typical solvent polarity range | High | High | High |
| Typical sample loading solvent | H₂O, buffers | H₂O, high salt | H₂O, buffers |
| Typical desorption solvent | Buffers, salt solutions | H₂O, low salt | H₂O, buffers, pH, competing reagents, heat, solvent polarity |
| Sample elution selectivity | Sample components most weakly ionized first | Sample components most polar first | Non-binding, low-binding, high-binding |
| Solvent change required to desorb | Increase ionic strength or increase retained compounds pH or decrease pH | Decrease ionic strength | Change pH, add competing reagent, change solvent polarity, increase heat |

Methods for Using the Extraction Columns

Generally the first step in an extraction procedure of the invention will involve introducing a sample solution containing an analyte of interest into a packed bed of extraction media, typically in the form of a column as described above. The sample can be conveniently introduced into the separation bed by pumping the solution through the column.

Columns of the invention can accommodate a variety of flow rates, and the invention provides methods employing a wide range of flow rates, oftentimes varying at different steps of the method. In various embodiments, the flow rate of liquid passing through the media bed falls within a range having a lower limit of 0.01 mL/min, 0.05 mL/min, 0.1 mL/min, 0.5 mL/min, 1 mL/min, 2 mL/min, or 4 mL/min and upper limit of 0.1 mL/min, 0.5 mL/min, 1 mL/min, 2 mL/min, 4 mL/min, 6 mL/min, 10 mL/min or greater. For example, some embodiments of the invention involve passing a liquid though a packed bed of media having a volume of less than 100 µL at a flow rate of between about 0.1 and about 4 mL/min, or between about 0.5 and 2 mL/min, e.g., a small packed bed of extraction media as described elsewhere herein. In another example, other embodiments of the invention involve passing a liquid though a packed bed of media having a volume of less than 25 µL at a flow rate of between about 0.1 and about 4 mL/min, or between about 0.5 and 2 mL/min.

In some cases, it is desirable to perform one or more steps of a purification process at a relatively slow flow rate, e.g., the loading and/or wash steps, to maximize binding of an analyte of interest to an extraction medium. To facilitate such methods, in certain embodiments the invention provides a pipette comprising a body; a microprocessor; an electrically driven actuator disposed within the body, the actuator in communication with and controlled by the microprocessor; a displacement assembly including a displacing piston moveable within one end of a displacement cylinder having a displacement chamber and having another end with an aperture, wherein said displacing piston is connected to and controlled by said actuator; and a pipette tip in communication with said aperture, wherein the microprocessor is programmable to cause movement of the piston in the cylinder at a rate that results in drawing a liquid into the pipette tip at a desired flow when the tip is in communication with the liquid. The flow rate can be relatively slow, such as the slow flow rates described above, e.g., between about 0.1 and 4 mL/min.

The pipette tip can be a pipette tip column of the invention, e.g., a pipette tip comprising a tip body having an open upper end, an open lower end, and an open channel between the upper and lower ends of the tip body; a bottom frit bonded to and extending across the open channel; a top frit bonded to and extending across the open channel between the bottom frit and the open upper end of the tip body, wherein the top frit, bottom frit, and column body define a media chamber; and a bed of media positioned inside the media chamber.

In some embodiments, the microprocessor is external to the body of the pipettor, e.g., an external PC programmed to control a sample processing procedure. In some embodiments the piston is driven by a motor, e.g., a stepper motor.

The invention provides a pipettor (such as a multi-channel pipettor) suitable for acting as the pump in methods such as those described above. In some embodiments, the pipettor comprises an electrically driven actuator. The electrically driven actuator can be controlled by a microprocessor, e.g., a programmable microprocessor. In various embodiments the microprocessor can be either internal or external to the pipettor body. In certain embodiments the microprocessor is programmed to pass a pre-selected volume of solution through the bed of media at a pre-selected flow rate. The back pressure of a column will depend on the average bead size, bead size distribution, average bed length, average cross sectional area of the bed, back pressure due to the frit and viscosity of flow rate of the liquid passing through the bed. For a column described in this application, the backpressure at 2 mL/min flow rate ranged from 0.05 to 2 psi.

Sometimes in order to improve recovery it is desirable to pass the desorption solvent through the extraction bed multiple times, e.g., by repeatedly aspirating and discharging the desorption solvent through the extraction bed and lower end of the column. Step elutions can be performed to remove materials of interest in a sequential manner. Air may be introduced into the bed at this point (or at any other point in the procedure), but because of the need to control the movement of the liquid through the bed, it is not preferred.

The desorption solvent will vary depending upon the nature of the analyte and extraction media. In some cases desorption is achieved by a change in pH or ionic strength, e.g., by using low pH or high ionic strength desorption solution. A suitable desorption solution can be arrived at using available knowledge by one of skill in the art.

Often it is desirable to automate the method of the invention. For that purpose, the subject invention provides a device for performing the method comprising a column containing a packed bed of extraction media, a pump attached to one end of said column, and an automated means for actuating the pump.

The automated means for actuating the pump can be controlled by software. This software controls the pump, and can be programmed to introduce desired liquids into a column, as well as to evacuating the liquid by the positive introduction of gas into the column if so desired.

For example, in certain embodiments the invention provides a general method for passing liquid through a packed-bed pipette tip column comprising the steps of:
a) providing a first column comprising:
   i. a column body having an open upper end for communication with a pump, a first open lower end for the uptake and dispensing of fluid, and an open passageway between the upper and lower ends of the column body;
   ii. a bottom frit attached to and extending across the open passageway;
   iii. an optional top frit attached to and extending across the open passageway between the bottom frit and the open upper end of the column body, wherein the top frit, bottom frit, and surface of the passageway define a media chamber;
   iv. a first packed bed of media positioned inside the media chamber;
   v. a first head space defined as the section of the open passageway between the open upper end and the top frit, wherein the head space comprises a gas having a first head pressure; and
   vi. a pump sealingly attached to the open upper end, where actuation of the pump affects the first head pressure, thereby causing fluid to be drawn into or expelled from the bed of media;
b) contacting said first open lower end with a first liquid;
c) actuating the pump to draw the first liquid into the first open lower end and through the first packed bed of media; and
d) actuating the pump to expel at least some of the first liquid through the first packed bed of media and out of the first open lower end.

In certain embodiments, the invention further comprises the following steps subsequent to step (d):
e) contacting said first open lower end with a second liquid, which is optionally the same as the first liquid;
f) actuating the pump to draw second liquid into the first open lower end and through the first packed bed of media; and
g) actuating the pump to expel at least some of the second liquid through the first packed bed of media and out of the first open lower end.

In a number of embodiments, the above-described method further comprise the steps of:
h) providing a second column comprising:
   i. a column body having an open upper end for communication with a pump, a second open lower end for the uptake and dispensing of fluid, and an open passageway between the upper and lower ends of the column body;
   ii. a bottom frit attached to and extending across the open passageway;
   iii. an optional top frit attached to and extending across the open passageway between the bottom frit and the open upper end of the column body, wherein the top frit, bottom frit, and surface of the passageway define a media chamber;
   iv. a second packed bed of media positioned inside the media chamber;
   v. a second head space defined as the section of the open passageway between the open upper end and the top frit, wherein the head space comprises a gas having a second head pressure; and
   vi. a pump sealingly attached to the second open upper end, where actuation of the pump affects the second head pressure, thereby causing fluid to be drawn into or expelled from the second packed bed of media;
i) contacting said second open lower end with a third liquid, which is optionally the same as the first liquid;
j) actuating the pump to draw the third liquid into the second open lower end and through the second packed bed of media;
k) actuating the pump to expel at least some of the third liquid through the second packed bed of media and out of the second open lower end.
l) contacting said second open lower end with a fourth liquid, which is optionally the same as the third liquid;
m) actuating the pump to draw fourth liquid into the second open lower end and through the second packed bed of media; and
n) actuating the pump to expel at least some of the fourth liquid through the second packed bed of media and out of the second open lower end The various embodiments described above that involve adjusting or controlling head pressure are particularly useful in embodiments of the invention that involve the use of automated or robotic liquid handling systems, e.g., automated multichannel pipettors. Thus, the various columns discussed can be different columns use simultaneously on a multichannel automated system, or in some cases different columns used sequentially on the same channel.

Multiplexing

In some embodiments of the invention, a plurality of columns is run in a parallel fashion, e.g., multiplexed. This allows for the simultaneous, parallel processing of multiple samples. A description of multiplexing of extraction capillaries is provided in U.S. patent application Ser. Nos. 10/434,713 and 10/733,534, and the same general approach can be applied to the columns and devices of the subject invention.

Multiplexing can be accomplished, for example, by arranging the columns in parallel so that fluid can be passed through them concurrently. When a pump is used to manipulate fluids through the column, each column in the multiplex array can have its own pump, e.g., syringe pumps activated by a common actuator. Alternatively, columns can be connected to a common pump, a common vacuum device, or the like. In another example of a multiplex arrangement, the plurality of columns is arranged in a manner such that they can be centrifuged, with fluid being driven through the columns by centrifugal force.

In one embodiment, sample can be arrayed from an extraction column to a plurality of predetermined locations, for example locations on a chip or microwells in a multi-well plate. A precise liquid processing system can be used to dispense the desired volume of eluent at each location. For example, an extraction column containing bound analyte takes up 50 μL of desorption solvent, and 1 μL drops are spotted into microwells using a robotic system such as those commercially available from Zymark (e.g., the SciClone sample handler), Tecan (e.g., the Genesis NPS, Aquarius or TeMo) or Cartesian Dispensing (e.g., the Honeybee benchtop system), Packard (e.g., the MiniTrak5, Evolution, Platetrack, or Apricot), Beckman (e.g., the FX-96) and Matrix (e.g., the Plate Mate 2 or SerialMate). This can be used for high-throughput assays, crystallizations, etc.

The extraction process can be automated, for example by using software to program the computer controller to control the pumping, e.g., the volumes, flow rates, delays, and number of cycles.

In some embodiments, the invention provides a multiplexed extraction system comprising a plurality of extraction columns of the invention, e.g., low dead volume pipette tip columns having small beds of packed gel resins. The system can be automated or manually operated. The system can include a pump or pump in operative engagement with the extraction columns, useful for pumping fluid through the columns in a multiplex fashion, i.e., concurrently. In some embodiments, each column is addressable. The term "addressable" refers to the ability of the fluid manipulation mechanism, e.g., the pumps, to individually address each column. An addressable column is one in which the flow of fluid through the column can be controlled independently from the flow through any other column which may be operated in parallel. In practice, this means that the pumping means in at least one of the extraction steps is in contact and control of each individual column independent of all the other columns. For example, when syringe pumps are used, i.e., pumps capable of manipulating fluid within the column by the application of positive or negative pressure, then separate syringes are used at each column, as opposed to a single vacuum attached to multiple syringes. Because the columns are addressable, a controlled amount of liquid can be accurately manipulated in each column. In a non-addressable system, such as where a single pump is applied to multiple columns, the liquid handling can be less precise. For example, if the back pressure differs between multiplexed columns, then the amount of liquid entering each column and/or the flow rate can vary substantially in a non-addressable system. Various embodiments of the invention can also include samples racks, instrumentation for controlling fluid flow, e.g., for pump control, etc. The controller can be manually operated or operated by means of a computer. The computerized control is typically driven by the appropriate software, which can be programmable, e.g., by means of user-defined scripts.

The invention also provides software for implementing the methods of the invention. For example, the software can be programmed to control manipulation of solutions and addressing of columns into sample vials, collection vials, for spotting or introduction into some analytical device for further processing.

The invention also includes kits comprising one or more reagents and/or articles for use in a process relating to solid-phase extraction, e.g., buffers, standards, solutions, columns, sample containers, etc.

Step and Multi-Dimensional Elutions

In some embodiments of the invention, desorption solvent gradients, step elutions and/or multidimensional elutions are performed.

The use of gradients is well known in the art of chromatography, and is described in detail, for example in a number of the general chromatography references cited herein. As applied to the extraction columns of the invention, the basic principle involves adsorbing an analyte to the extraction media and then eluting with a desorption solvent gradient. The gradient refers to the changing of at least one characteristic of the solvent, e.g., change in pH, ionic strength, polarity, or the concentration of some agent that influence the strength of the binding interaction. The gradient can be with respect to the concentration of a chemical that entity that interferes with or stabilizes an interaction, particularly a specific binding interaction. For example, where the affinity binding agent is an immobilized metal, the gradient can be in the concentration of imidazole, EDTA, etc. In some embodiments, the result is fractionation of a sample, useful in contexts such as gel-free shotgun proteomics.

As used herein, the term "dimension" refers to some property of the desorption solvent that is varied, e.g., pH, ionic strength, etc. An elution scheme that involves variation of two or more dimensions, either simultaneously or sequentially, is referred to as a multi-dimensional elution.

Gradients used in the context of the invention can be step elutions. In one embodiment, two or more elution steps are performed using different desorption solvents (i.e., elution solvents) that vary in one or more dimensions. For example, the two or more solvents can vary in pH, ionic strength, hydrophobicity, or the like. The volume of desorption solution used in each dimension can be quite small, and can be passed back and forth through the bed of extraction media multiple times and at a rate that is conducive to maximal recovery of desired analyte. Optionally, the column can be purged with gas prior between steps in the gradient.

A multi-dimensional extraction involves varying at least two desorption condition dimensions.

In a typical example, a stepwise elution is performed in one dimension, collecting fractions for each change in elution conditions. For example, a stepwise increase in ionic strength could be employed where the extraction phase is based on ion exchange. The eluted fractions are then introduced into a second extraction column (either directly or after collection into an intermediate holding vessel) and in this case separated in another dimension, e.g., by reverse-phase, or by binding to an affinity binding group such as avidin or immobilized metal.

In some embodiments, one or more dimensions of a multidimensional extraction are achieved by means other than an extraction column of the invention. For example, the first dimension separation might be accomplished using conventional chromatography, electrophoresis, or the like, and the fractions then loaded on an extraction column for separation in another dimension.

Note that in many cases the elution of a protein will not be a simple on-off process. That is, some desorption buffers will result in only partial release of analyte. The composition of the desorption buffer can be optimized for the desired outcome, e.g., complete or near complete elution. Alternatively, when step elution is employed two or more successive steps in the elution might result in incremental elution of fraction of an analyte. These incremental partial elution can be useful in characterizing the analyte, e.g., in the analysis of a multi-protein complex as described below.

In order to expel all liquid from a pipette tip column, the syringe plunger or displacing piston must be able to displace enough chamber volume to achieve the required positive head pressure. Consider the case where a displacing piston starts at a given starting position corresponding to a starting chamber volume. The piston is retracted, increasing the chamber volume and resulting in the uptake of liquid. The piston is then extended back to the starting position, reducing the chamber volume to the starting chamber volume. In some cases, due for example to the surface tension and other effects described herein, the extension of the piston back to the starting position is insufficient to expel all of the liquid from the tip as desired. It is thus necessary to extend the piston beyond the starting position to expel the full amount of liquid. This is impossible if the starting position of the piston is at the fully extended position, i.e., the typical starting point, where the chamber volume is at its minimum. Thus, in some embodiments of invention, the piston (or its equivalent, such as the plunger in a syringe) is retracted to some extent from the fully extended position before beginning to take up any liquid, i.e., the starting position is displaced from the fully extended position, and hence the chamber volume is greater than the minimum. This is advantageous in that it allows the piston to be extended beyond the starting point during liquid expulsion, allowing for the creation of greater positive head pressure to expel all of the liquid from the column as desired. The greater the displacement of the starting position from the fully extended position, the greater the head pressure that can be created at the end of the extension step. The degree of displacement should be enough to compensate for backpressures encountered in the particular column system at hand, and can be determined empirically or calculated based on the properties of the column, sample liquid, pump system, etc.

Thus, in one embodiment the invention provides a method of purifying an analyte comprising the steps of: (a) providing a column comprising: a column body having an open upper end for communication with a pump, an open lower end for the uptake and dispensing of fluid, and an open passageway between the upper and lower ends of the column body; a bottom frit attached to and extending across the open passageway; a top frit attached to and extending across the open passageway between the bottom frit and the open upper end of the column body, wherein the top frit, bottom frit, and surface of the passageway define a media chamber; a packed bed of media positioned inside the media chamber; a head space defined as the section of the open passageway between the open upper end and the top frit, wherein the head space comprises a gas having a head pressure; and a pump (e.g., a pipettor or syringe) sealingly attached to the open upper end, wherein the pump includes a linear actuator (which can be controlled by an electrically driven microprocessor) and, connected to and controlled by the linear actuator, a displacement assembly including a displacing piston moveable within one end of a displacement cylinder having a displacement chamber and having an end with an aperture in communication with the head space; (b) positioning the piston at a starting position that is displaced from a full-extended position that corresponds to a minimum displacement chamber volume, wherein the starting position is sufficiently displaced from the fully-extended position such that full extension of the piston will cause full expulsion of liquid from the column during an expulsion step in the process (full expulsion being defined as the expulsion of all liquid or some of the liquid to the extent desired by the operator of the method); (c) positioning the open lower end into a liquid (either before, after, or concurrently with step (b)); retracting the piston to draw liquid through the open lower end and into the packed bed of media; and (d) extending the piston beyond the starting point, thereby expelling the liquid through the packed bed of media and out of the open lower end.

Positioning Tips for Use in Multiplexed Processes

In some embodiments, methods of the invention involve multiplexed extraction by means of a plurality of pipette tip columns and a multi-channel pipettor. The methods can involve drawing liquid from a well in a multi-well plate. The volume of liquid can be relatively small, e.g., on the order of 10 μL or less of desorption solution, and it is often important that substantially the entire volume of liquid is taken up by each of the tips. To achieve this, it is critical that the open lower end of each pipette tip column is accurately placed at a position in each well that is in contact with the fluid and submerged at a depth such that substantially all of the liquid will be drawn into the tip upon application of sufficient negative pressure in the head space. Typically this position is near the center of a circular well, at a depth that is near the bottom of the well (within one to several millimeters) but preferably not in direct contact with the bottom. If the tip makes direct contact with the well surface, there is the danger that a seal might form between the tip and the well that will restrict flow of liquid into and/or out of the tip. However, contact between the tip and well bottom will not necessarily prevent or restrict flow into the tip, particularly if no seal is formed between the tip and well.

Figure 7:
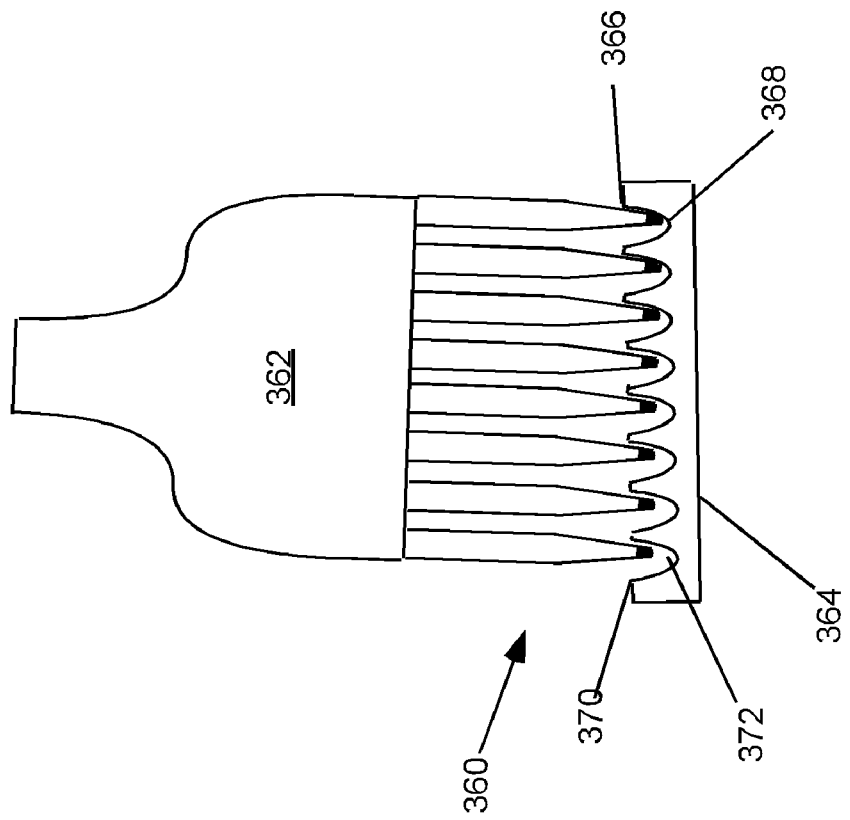

A problem that can arise in a multiplexed purification process is that it can be difficult to accurately position all of the tips on a multichannel pipettor such that each is at the optimal position in its corresponding well. For example, if the open lower ends of each tip are not positioned in substantially a straight line (for a linear configuration of tips) or a plane (for at two-dimensional array of tips), and that line (or plane) is not substantially parallel to the bottoms of the corresponding array of wells in a plate, then it will be very difficult to simultaneously position each tip at its optimal location. This is illustrated in FIG. 7, which depicts eight pipette tip columns 360 attached to an eight channel pipettor 362. The tips are positioned in the wells of a multi-well plate 364, over and close to the bottom of the wells. Because the pipettor is at a slight angle in relation to the plate, the tip at the far right 366 is making contact with the bottom of the well 368, which can restrict flow of liquid through the tip. On the other hand, the tip to the far left 370 is positioned too high, and will not be able to fully draw up a small aliquot of liquid from the bottom of the well 372.

Thus, in one embodiment, the invention provides a method for accurately positioning a plurality of tip columns into the wells of a microwell plate. The method as applied to a linear configuration of pipette tip columns is exemplified in FIG. 25. In this case, positioning tips 380 that extend slightly longer than the pipette columns are positioned at either end of the row of pipette tip columns, in an arrangement reminiscent of "vampire teeth." In operation, the positioning tips are positioned so that both rest against the bottom of their corresponding wells 382. The pipette tip columns internal to the two positioning tips are elevated from the bottom of their wells be a distance equal to the distance the positioning tips extend beyond the ends of the pipette tips. Thus, by adjusting the length of the positioning tips it is possible to position the internal tips 384 at any desired distance from the bottom of their corresponding wells. The positioning tips greatly simplify and stabilize the positioning of the pipette tips at a predetermined and uniform distance from the well bottoms.

Figure 8:
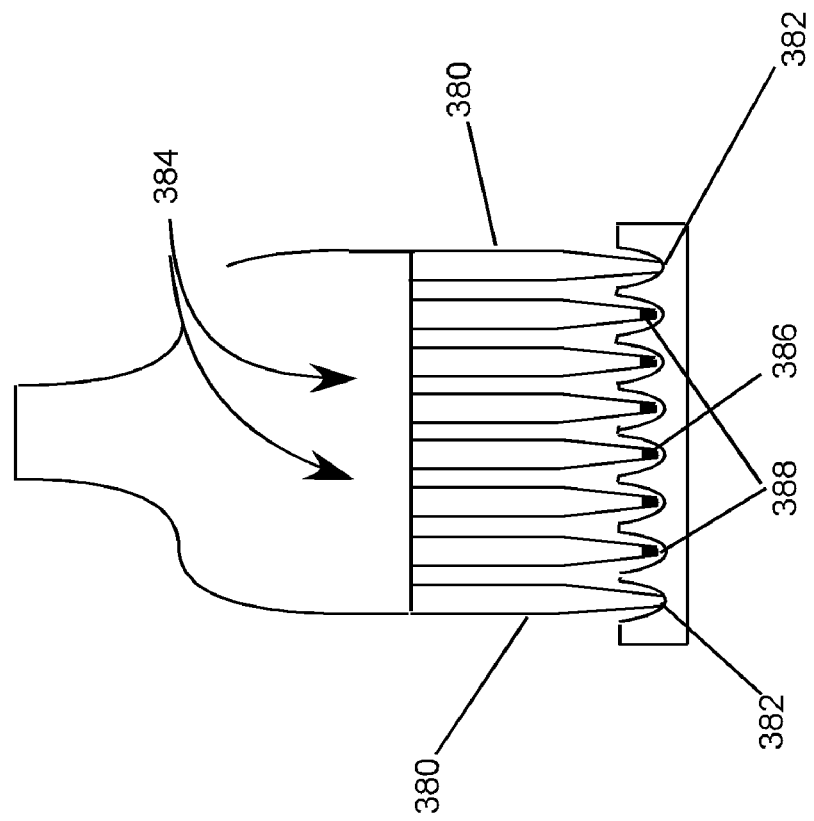
FIGS. 7 through 10 depict a method for positioning pipette tip columns in a multiplexed extraction process.

Note that as depicted in FIG. 8, there are two positioning tips, one at either end of the row of tips. In alternative embodiments a single positioning tip could be used, e.g., at a position near the center of the row like tip 386. In general, the use of a single positioning tip will not afford the stability and accuracy of a multi-positioning tip format, but it will be better than not using a positioning tip at all and in some instances will be sufficient.

Alternatively, more than two positioning tips could be used, although normally two is sufficient for a linear arrangement of pipette tips. However, if the row of tips is significantly longer than eight tips in length, then it might be the case that the additional stability provided by more than two positioning tips is beneficial.

Note that whether one or more tips are used, it is not necessary that the positioning tips take any particular position relative to the tip columns. For example, the arrangement of FIG. 8 could be varied such that the positioning tips are positioned at positions 388, and positions 380 might in this scenario be occupied by functional tip columns.

Figure 9:
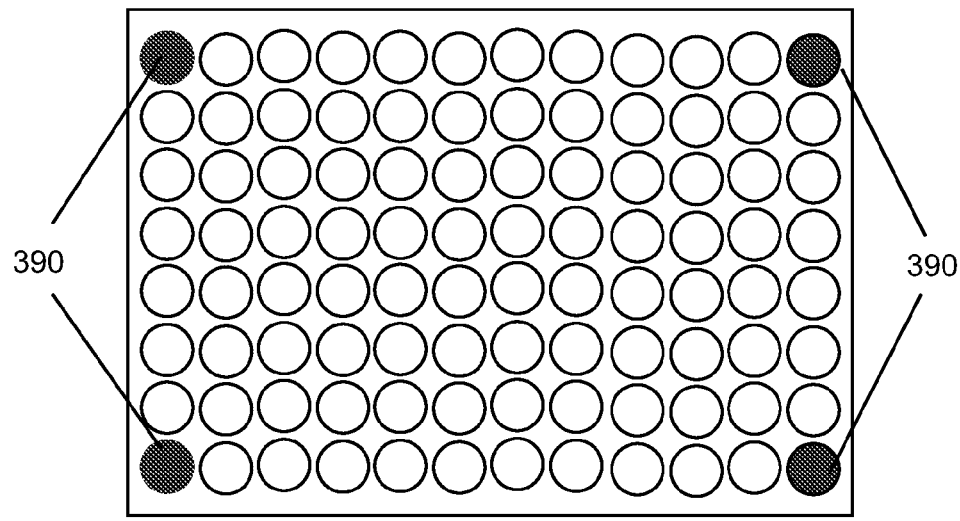
Figure 10:
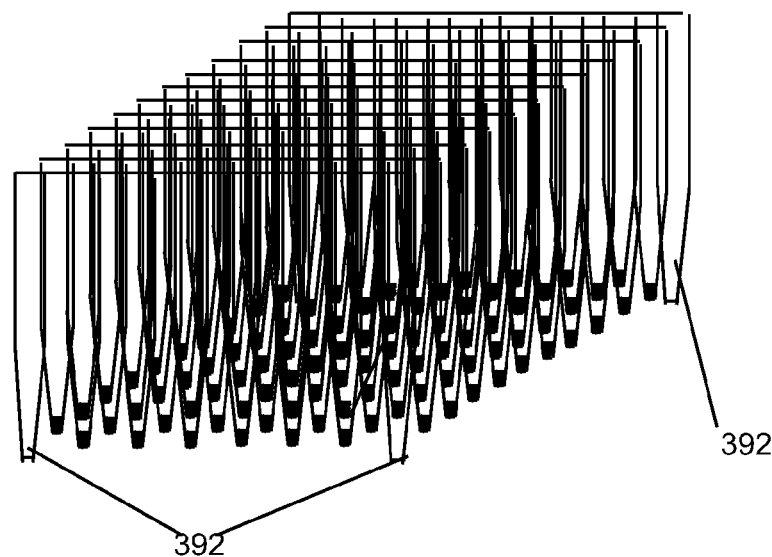

The positioning tips will make contact with a reference point that is located at a fixed, predetermined location relative to the well bottoms corresponding to pipette tip columns. For example, the reference point can be a well bottom not being used in an extraction process. For example, FIG. 9 depicts a 96 well plate. The four corner wells 390 are not used to hold liquid but are rather used as reference points; positioning tips located at the four corners of the two-dimensional array of pipette tip columns in FIG. 10 are brought into contact with the bottoms of the wells 390 to correctly position the pipette tip columns in the corresponding wells of the plate.

The method is also suitable for use with a two-dimensional array of tips, such as on a multi-channel pipettor having more than one row of tip columns, e.g., a 96 channel pipettor that is part of a robotic fluid handling system. For example, FIG. 10 depicts an 8×12 array of 96 pipette tip columns and positioning tips. In this particular example, the positioning tips are at the corners of the array 392. As was the case with linear configurations of tips, in two-dimensional arrays there are a variety of alternative options for the number and location of the positioning tips. For example, in a preferred embodiment four positioning tips are used, one at each corner of the array of tips. Alternatively, more or less than four positioning tips could be used, e.g., two tips, one at each of two opposite corners, or a single tip located at a corner or internal position in the array.

Thus, in certain embodiments the invention provides a general method of positioning a pipette tip column in relative to a well bottom comprising the steps of: (a) providing a pipetting system comprising: (i) a pipettor; (ii) a pipette tip column having an open upper end operatively engaged with said pipettor and an open lower end for passing solution through the pipette tip column; and (iii) a positioning tip attached to said pipettor, said positioning tip having a proximal end attached to the pipettor and a distal end positioned at a fixed, predetermined location relative to the open lower end of the pipette tip column; and (b) positioning the pipetting system so that: (i) the distal end of the positioning tip makes contact with a reference point, wherein said reference point is located at a fixed, predetermined location relative to a well having a well bottom; and (ii) the open lower end of the pipette tip column is positioned over the well bottom.

The pipetting system can be part of a robotic liquid handling system.

In certain embodiments the well contains a liquid, e.g., a sample, wash or desorption solution. In certain embodiments the pipetting system is positioned so that the open lower end of the pipette tip column makes contact with the liquid, and the pipettor is activated to draw liquid through the open lower end and into the pipette tip column.

In certain embodiments the pipettor is a multi-channel pipettor.

Particularly in cases where the pipettor is a multi-channel pipettor, the pipetting system can comprise a plurality of pipette tip columns, each pipette tip column having an open upper end operatively engaged with said pipettor and an open lower end for passing solution through the pipette tip column, wherein the pipetting system is positioned so that: (i) the distal end of the positioning tip makes contact with a reference point, wherein said reference point is located at a fixed, predetermined location relative to a well having a well bottom; and (ii) the open lower end of each of the pipette tip column is positioned over a well bottom of one of the plurality of wells.

In certain embodiments positioning tip is a pipette tip, a pipette tip column, or some other object capable of attachment to the pipettor. The attachment can be transient, or the positioning tip can be permanently affixed to the pipettor or even an integral component of the pipettor.

In certain embodiments the wells are all elements of a multi-well plate. e.g., microwells.

In certain embodiments of the invention involving a multi-well plate, the reference point can be located on the multi-well plate, e.g., the reference point can be the bottom of a well of the multi-well plate.

In certain embodiments, a plurality of positioning tips is used, each positioning tip making contact with a reference point located at a fixed, predetermined location relative to the plurality of wells.

In certain embodiments, the volume of liquid in the wells is relatively low, e.g., in a range having a lower limit of 5 µL or 10 µL, and an upper limit of 20 µL, 30 µL, 50 µL, 100 µL, 200 µL or even 500 µL. For example, in certain embodiments the volume of liquid in the wells is of between 1 and 100 µL, or 1 and 20 µL, or 5 and 20 µL.

In certain embodiments, the open lower end of the pipette tip column is positioned close enough to the well bottom such that upon activation of the pipettor substantially all of the liquid is drawn through the open lower end and into the pipette tip column, but not so close as to form a seal with the well bottom.

The open lower end of the pipette tip column is typically positioned relatively close to the corresponding well bottom, e.g., within a range having a lower limit of about 0.05 mm, 0.1 mm, 0.2 mm, 0.3 mm, 0.4 m, 0.5 mm, 1 mm, 2 mm, 3 mm, 4 mm, or 5 mm from the bottom of the well, and an upper limit of 0.3 mm, 0.4 m, 0.5 mm, 1 mm, 2 mm, 3 mm, 4 mm, 5 mm, 6 mm, 7 mm, 8 mm, 8 mm or 10 mm of the well bottom. For example, in some embodiments the open lower end of a pipette tip column is positioned with between 0.05 and 2 mm from a well bottom, or between 0.1 and 1 mm from a well bottom. The term "well bottom" does not necessarily refer to the absolute bottom of a well, but to the point where the tip makes contact with the well when the tip is lowered to its full extent into the well, i.e., a point where the tip can seal with the well surface. For example, in some microwell plate formats the wells taper down to an inverted conical shape, so a typical tip column will not be able to make contact with the absolute bottom of the well.

In certain embodiments, the positioning tips are longer than the pipette tip columns. The difference in length between positioning tips and pipette tip columns can result in accurately locating the ends of the pipette tip columns at a desired distance from the bottoms of the corresponding wells. The difference in length between positioning tips and pipette tip columns can be relatively small, e.g. in a range having a lower limit of 0.1 mm, 0.2 mm, 0.5 mm, 1 mm or 2 mm and an upper limit of 1 mm, 2 mm, 3 mm, 4 mm, 5 mm 6 mm, 7 mm, 8 mm, 8 mm or 10 mm. For example, in certain embodiments the positioning tips are between 1 and 10 mm longer than the pipette tip columns.

In certain embodiments, a plurality of pipette tip columns and positioning tips are attached to a multi-channel pipettor in a linear configuration. For example, the positioning tips can be positioned at the two ends of the linear configuration of pipette tip columns and positioning tips, e.g., see FIGS. 7 and 8.

In certain embodiments, a plurality of pipette tip columns and positioning tips are attached to a multi-channel pipettor in a two-dimensional array. The two-dimensional array can comprise four corners, with positioning tips are positioned at two or more of the corners. For example, the positioning tips can be positioned at four corners of a two-dimensional array, e.g., see FIGS. 9 and 10.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

Evaluation of an 80 µL Bed Volume Pipette Tip Column Containing a PhyNexus Resin for Purification of Plasmid from Eukaryotic Cells In this example, the performance of 80 µL, bed volume pipette tip columns is evaluated. The pipette tip column was constructed from a 200 µL, pipette tip (Tecan) and is packed with a silica-based particle resin. These columns, buffer conditions and column processing procedures are tested for the recovery of DNA plasmids from complicated samples. The yield and quality are assessed by UV spectrometry and agarose gel electrophoresis.

Samples are prepared by first growing a single yeast colony in 25 mL media supplemented with the appropriate carbon source to propagate the DNA vector. The liquid culture is incubated at 30° C. with shaking until the media becomes turbid. The culture is divided into equal aliquots and subject to centrifugation 5,000×g for 15 minutes to pellet the yeast. The supernatant is discarded and the pellets are lysed by mortar and pestle, using liquid nitrogen and resuspended buffer.

To purify the DNA plasmids from the lysed yeast cells, the pipette tip columns are processed by the ME semi-automated purification system (PhyNexus). The columns are equilibrated with 200 µL 7M guanidinium-HCl by performing one cycle of back-and-forth flow at 500 µL/min and 20 second pauses at the end of each aspirate and each dispense step.

The yeast lysate is subjected to pipette tip column processing for capture of the plasmid DNA by using at least 24 back-and-forth cycles of 250 µL/min and 20 second pauses after the end of each aspirate and dispense step.

Following plasmid capture on the pipette tip column, the columns are washed with 200 µL wash 1 buffer consisting of 10 mM Tris-HCl pH 6.6, 5M guanidinium-HCl and 30% ethanol. This is followed by a second wash in wash 2 buffer consisting of 10 mM Tris-HCl pH 7.5 and 80% ethanol. Both wash procedures proceed by one cycle of back-and-forth flow at 500 µL/min and 20 second pauses at the end of each aspirate and expel step. A blow out step is incorporated to remove all residual wash buffer from the resin bed.

DNA plasmid is released from the column with 300 µL elution buffer consisting of water. The procedure to release the DNA is 8 back-and-forth cycles of 250 µL/min and 20 second pauses after the end of each aspirate and dispense step.

DNA is quantified by absorbance at 260 nm. The quality of the DNA is assessed by the shape of the absorbance spectrum, the ration of absorbance at 260 to absorbance at 280 nm, agarose gel electrophoresis and transformation efficiency.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such preferred embodiments.

What is claimed is:

1. A method of extracting plasmid DNA from an unclarified lysate, comprising the steps of:
  a. providing an unclarified cell lysate;
  b. providing at least one pipette tip column, wherein the pipette tip column is comprised of
    i) a column body having an open upper end, an open lower end, and an open channel between the upper and lower ends of the column body, wherein the column body is comprised of a modified pipette tip;
    ii) a bottom frit extending across the open channel, said bottom frit having a thickness in the range of 20 µm to 1000 µm and a pore size in the range of 50 µm to 250 µm; and
    iii) a bed of extraction media positioned inside the open channel and in contact with the bottom frit;
  c. passing the unclarified cell lysate through the pipette tip column wherein the plasmid DNA is captured by the bed of extraction media;
  d. passing wash solution through the pipette tip column; and
  e. eluting the plasmid DNA by passing a desorption solvent through the pipette tip column.

2. The method of claim 1, wherein the upper end of the column is operatively attached to a pump, and wherein the unclarified cell lysate, wash solution and desorption solution are passed through the column by aspirating and expelling through the open lower end of the column.

3. The method of claim 2, wherein the unclarified cell lysate, wash solution or desorption solution are passed back and forth through the bed of extraction media more than once.

4. The method of claim 3, wherein the method is automated and wherein the method is performed in parallel on a plurality of pipette tip columns.

5. A method of extracting plasmid DNA from an unclarified lysate, comprising the steps of:
  a. providing an unclarified cell lysate;
  b. providing at least one pipette tip column, wherein the pipette tip column is in operative engagement with a pipette or liquid handler, and wherein the pipette tip column is comprised of
    i) a column body having an open upper end, an open lower end, and an open channel between the upper and lower ends of the column body, wherein the column body is comprised of a modified pipette tip;
    ii) a bottom frit extending across the open channel, said bottom frit having a pore size sufficiently large to allow cell debris to flow through the frit; and iii) a bed of extraction media positioned inside the open channel and in contact with the bottom frit;
c. passing the unclarified cell lysate back and forth repeatedly through the pipette tip column;
d. passing wash solution through the pipette tip column; and
e. eluting the plasmid DNA by passing a desorption solvent through the pipette tip column.

6. The method of claim 5, wherein the wash solution or the desorption solution are passed back and forth through the bed of extraction media more than once.

7. The method of claim 6, wherein the method is automated and wherein the method is performed in parallel on a plurality of pipette tip columns.

* * * * *

UNITED STATES PATENT AND TRADEMARK OFFICE
CERTIFICATE OF CORRECTION

PATENT NO.         : 8,377,715 B2                                    Page 1 of 1
APPLICATION NO.    : 12/767659
DATED              : February 19, 2013
INVENTOR(S)        : Chris Suh et al.

It is certified that error appears in the above-identified patent and that said Letters Patent is hereby corrected as shown below:

In The Specification

Column 10, line 12, "herein are" should read -- herein is --.

Column 22, line 29, "cells lysates" should read -- cell lysates --.

Signed and Sealed this
Nineteenth Day of July, 2016

Michelle K. Lee
*Director of the United States Patent and Trademark Office*